United States Patent
Prugh et al.

(10) Patent No.: US 11,953,881 B2
(45) Date of Patent: Apr. 9, 2024

(54) PROPERTY CONTROL AND CONFIGURATION BASED ON FLOOR CONTACT MONITORING

(71) Applicant: Alarm.com Incorporated, Tysons, VA (US)

(72) Inventors: Alexander Prugh, Washington, DC (US); Johnathan Michael Carone, McLean, VA (US); Donald Gerard Madden, Columbia, MD (US); Mary Melissa Kalagher, Reston, VA (US); Daniel John Koniar, Bloomington, MN (US); Liyu Yao, McLean, VA (US); Martin Logan Elliott, McLean, VA (US); John Zhang, Chicago, IL (US); William Wireko Mensah, Fairfax, VA (US)

(73) Assignee: Alarm.com Incorporated, Tysons, VA (US)

( * ) Notice: Subject to any disclaimer, the term of this patent is extended or adjusted under 35 U.S.C. 154(b) by 750 days.

(21) Appl. No.: 16/855,830

(22) Filed: Apr. 22, 2020

(65) Prior Publication Data
US 2020/0341457 A1 Oct. 29, 2020

Related U.S. Application Data

(60) Provisional application No. 62/837,466, filed on Apr. 23, 2019.

(51) Int. Cl.
*G08B 13/10* (2006.01)
*A61B 5/00* (2006.01)
(Continued)

(52) U.S. Cl.
CPC ........ *G05B 19/4155* (2013.01); *A61B 5/1038* (2013.01); *A61B 5/1074* (2013.01);
(Continued)

(58) Field of Classification Search
CPC .......................... G08B 21/043; G08B 21/0407
See application file for complete search history.

(56) References Cited

U.S. PATENT DOCUMENTS 7,382,267 B2 * 6/2008 Brendley ............... G08B 13/10
340/541
7,994,928 B2 8/2011 Richmond
(Continued)

FOREIGN PATENT DOCUMENTS

EP 2111791 10/2009
JP 2006195881 7/2006
(Continued)

OTHER PUBLICATIONS

EP Partial Supplementary European Search Report in European Appln. No. 20794188.1, dated May 6, 2022, 17 pages.
(Continued)

*Primary Examiner* — Qutbuddin Ghulamali
(74) *Attorney, Agent, or Firm* — Fish & Richardson P.C.

(57) ABSTRACT

A monitoring system that is configured to monitor a property is disclosed. The monitoring system includes a sensor that is configured to generate sensor data that indicates an attribute of the property; a floor sensor that is configured to generate floor sensor data that indicates an amount of pressure applied to a portion of a floor of the property; and a monitor control unit. The monitor control unit is configured to receive, from the sensor, the sensor data; receive, from the floor sensor, the floor sensor data; analyze the sensor data and the floor sensor data; and based on analyzing the sensor data and the floor sensor data, perform a monitoring system action.

32 Claims, 6 Drawing Sheets

(51) Int. Cl.

| | | |
|---|---|---|
| *A61B 5/103* | (2006.01) | |
| *A61B 5/107* | (2006.01) | |
| *A61B 5/11* | (2006.01) | |
| *G01G 19/44* | (2006.01) | |
| *G01L 1/14* | (2006.01) | |
| *G01L 1/22* | (2006.01) | |
| *G01L 1/24* | (2006.01) | |
| *G05B 19/4155* | (2006.01) | |
| *H04Q 9/00* | (2006.01) | |
| *G08B 13/196* | (2006.01) | |
| *G08B 29/18* | (2006.01) | |

(52) U.S. Cl.
CPC .......... *A61B 5/1117* (2013.01); *A61B 5/6889* (2013.01); *G01G 19/44* (2013.01); *G01L 1/142* (2013.01); *G01L 1/22* (2013.01); *G01L 1/242* (2013.01); *H04Q 9/00* (2013.01); *A61B 2503/12* (2013.01); *A61B 2505/07* (2013.01); *A61B 2562/0266* (2013.01); *G05B 2219/40062* (2013.01); *G08B 13/19695* (2013.01); *G08B 29/185* (2013.01); *H04Q 2209/823* (2013.01)

(56) References Cited

U.S. PATENT DOCUMENTS

| | | | |
|---|---|---|---|
| 9,691,240 B2 | 6/2017 | Bradford | |
| 2010/0171588 A1* | 7/2010 | Chutorash | G07C 9/30 340/5.71 |
| 2010/0305816 A1* | 12/2010 | Orlewski | B60R 21/01526 701/45 |
| 2016/0171588 A1* | 6/2016 | Linden | G06F 3/0482 705/26.7 |
| 2016/0203688 A1* | 7/2016 | Zitt | G08B 25/08 340/568.1 |
| 2016/0217664 A1* | 7/2016 | Bradford | H04Q 9/00 |
| 2018/0018509 A1 | 1/2018 | Zhang et al. | |
| 2020/0341457 A1* | 10/2020 | Prugh | G05B 19/4155 |

FOREIGN PATENT DOCUMENTS

| | | |
|---|---|---|
| KR | 101897065 | 9/2018 |
| WO | WO2016/118797 | 7/2016 |

OTHER PUBLICATIONS

PCT International Search Report and Written Opinion in International Application No. PCT/US2020/029651, dated Aug. 4, 2020, 10 pages.
Chaccour; Kabalan, "Elaborating the Actimetric Profile of Fall Sensitive Patients for Early Detection of Fall Incidents," Universite Bourgogne Franche-Comte, 2017, HAL archives-ouvertes, Submitted Aug. 31, 2018, 193 pages.
Daher et al., "Elder Tracking and Fall Detection System using Smart Tiles," IEEE Sensors Journal, ResearchGate, Nov. 2016, 12 pages.
Jideofor et al., "Intelligent Sensor Floor for Fall Prediction and Gait Analysis," CSE UTA, Technical Report CSE-2012-4, 8 pages.
Valtonen et al., "TileTrack: Capacitive Human Tracking Using Floor Tiles," 2009 IEEE International Conference on Pervasive Computing and Communications, Galveston, TX, Mar. 9-13, 2009, 10 pages.

* cited by examiner

PROPERTY CONTROL AND CONFIGURATION BASED ON FLOOR CONTACT MONITORING

CROSS-REFERENCE TO RELATED APPLICATION

This application claims the benefit of U.S. Application No. 62/837,466, filed Apr. 23, 2019, which is incorporated by reference.

TECHNICAL FIELD

This specification generally relates to property monitoring systems.

BACKGROUND

Many properties are equipped with monitoring systems that include sensors and connected system components.

SUMMARY

According to an innovative aspect of the subject matter described in this application, a monitoring system is configured to monitor a property. The monitoring system includes a sensor that is configured to generate sensor data that indicates an attribute of the property; a floor sensor that is configured to generate floor sensor data that indicates an amount of pressure applied to a portion of a floor of the property; and a monitor control unit. The monitor control unit is configured to: receive, from the sensor, the sensor data; receive, from the floor sensor, the floor sensor data; analyze the sensor data and the floor sensor data; and based on analyzing the sensor data and the floor sensor data, perform a monitoring system action.

Other embodiments of this and other aspects include corresponding systems, apparatus, and computer programs, configured to perform actions of methods encoded on computer storage devices. A system of one or more computers or other processing devices can be so configured by virtue of software, firmware, hardware, or a combination of them installed on the system that in operation cause the system to perform the actions. One or more computer programs can be so configured by virtue having instructions that, when executed by data processing apparatus, cause the apparatus to perform the actions.

These and other embodiments may each optionally include one or more of the following features.

In some implementations, the monitor control unit is configured to detect, based on analyzing the sensor data and the floor sensor data, one or more footsteps taken on the portion of the floor by a person; and generate footstep data, the footstep data including one or more of: a number of footsteps taken on the portion of the floor during a period of time; a path of footsteps taken on the portion of the floor during the period of time; a gait pattern of the person; a weight of the person; or a foot size of the person.

In some implementations, the monitor control unit is configured to: determine, based on analyzing the sensor data and the floor sensor data, that a person has fallen on the portion of the floor; and in response to determining that the person has fallen on the portion of the floor, perform the monitoring system action.

In some implementations, determining that the person has fallen on the portion of the floor includes: determining an impact pressure applied to the portion of the floor; and determining that the impact pressure applied to the portion of the floor exceeded a threshold impact pressure.

In some implementations, determining that the person has fallen on the portion of the floor includes: determining a distribution of the amount of pressure applied to the portion of the floor; determining that the distribution of the amount of pressure applied to the portion of the floor indicates that a person is prone on the floor; and determining that a length of time that the person is prone on the floor exceeds a threshold length of time.

In some implementations, the monitor control unit is configured to: determine, based on analyzing the sensor data and the floor sensor data, an occupancy of a portion of the property; determine that the occupancy of the portion of the property exceeds a threshold occupancy of the property; and in response to determining that the occupancy of the portion of the property exceeds the threshold occupancy of the property, perform the monitoring system action.

In some implementations, the monitor control unit is configured to: determine a base state of the portion of the floor, the base state including an amount of pressure applied to the portion of the floor by one or more inanimate objects in the absence of human activity; detect, based on analyzing the floor sensor data, a change in the amount of pressure applied to the portion of the floor in the absence of human activity; and based on detecting the change in the amount of pressure applied to the portion of the floor in the absence of human activity, determine that a location of one or more inanimate objects has changed.

In some implementations, the sensor includes a camera, a motion sensor, a microphone, a thermometer, a humidity sensor, a GPS tracker, or a water flow sensor.

In some implementations, the monitor control unit is configured to: determine an amount of pressure applied to the portion of the floor by a furnishing storing a plurality of items; detect, based on analyzing the floor sensor data, a reduction in the amount of pressure applied to the portion of the floor by the furnishing; based on detecting the reduction in the amount of pressure applied to the portion of the floor by the furnishing, determine that one or more of the plurality of items has been removed from the furnishing; and in response to determining that the one or more of the plurality of items has been removed from the furnishing, perform the monitoring system action.

In some implementations, the floor is located in a garage having a garage door operated by a garage door control device, and the monitor control unit is configured to: determine an amount of pressure applied to the portion of the floor by a vehicle; detect, based on analyzing the floor sensor data, an increase in the amount of pressure applied to the portion of the floor by the vehicle; based on detecting the increase in the amount of pressure applied to the portion of the floor by the vehicle, determine that a person has entered the vehicle; and in response to determining that the person has entered the vehicle, communicate an instruction to the garage door control device to open the garage door.

In some implementations, the floor sensor is integrated into a floor surface, the floor surface including one or more of a tile, a carpet, a mat, a floorboard, a pad, or an underlayment.

In some implementations, the floor of the property includes a plurality of tiles, and the floor sensor includes: a plurality of pressure sensors, each of the plurality of pressure sensors integrated into a respective tile of the plurality of tiles and configured to output a measured amount of pressure applied to the respective tile.

In some implementations, the floor sensor includes one or more of a strain gauge, a fiber optic sensor, or a capacitive sensor.

In some implementations, the amount of pressure applied to the portion of the floor of the property comprises an indication of either a presence or absence of pressure applied to the portion of the floor.

In some implementations, the monitoring system action includes activating one or more cameras to capture an image of an area of the property that includes the portion of the floor.

In some implementations, the monitoring system action includes: identifying, using image analysis, a presence of a person in the image; and determining, based on analyzing the floor sensor data, a weight of the person in the image.

In some implementations, the monitor control unit is configured to: determine, based on the footstep data, that the number of footsteps taken on the portion of the floor during the period of time deviates from an expected number of footsteps taken on the portion of the floor during the period of time; and communicate, to a user device of a user, a notification indicating that the number of footsteps taken on the portion of the floor during the period of time deviates from the expected number of footsteps taken on the portion of the floor during the period of time.

In some implementations, the monitoring system action is configured to: determine, based on the path of footsteps taken on the portion of the floor during the period of time, that the person is approaching an area of the property that is off limits to the person; and in response to determining that the person is approaching the area of the property that is off limits to the person, perform the monitoring system action.

In some implementations, determining that the person is approaching the area of the property that is off limits to the person includes: identifying, based on analyzing the sensor data, an identifiable feature of the person; retrieving, from a database, one or more identifiable features indicating access to the area of the property; and determining that the identifiable feature of the person does not match any of the one or more identifiable features indicating access to the area of the property.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
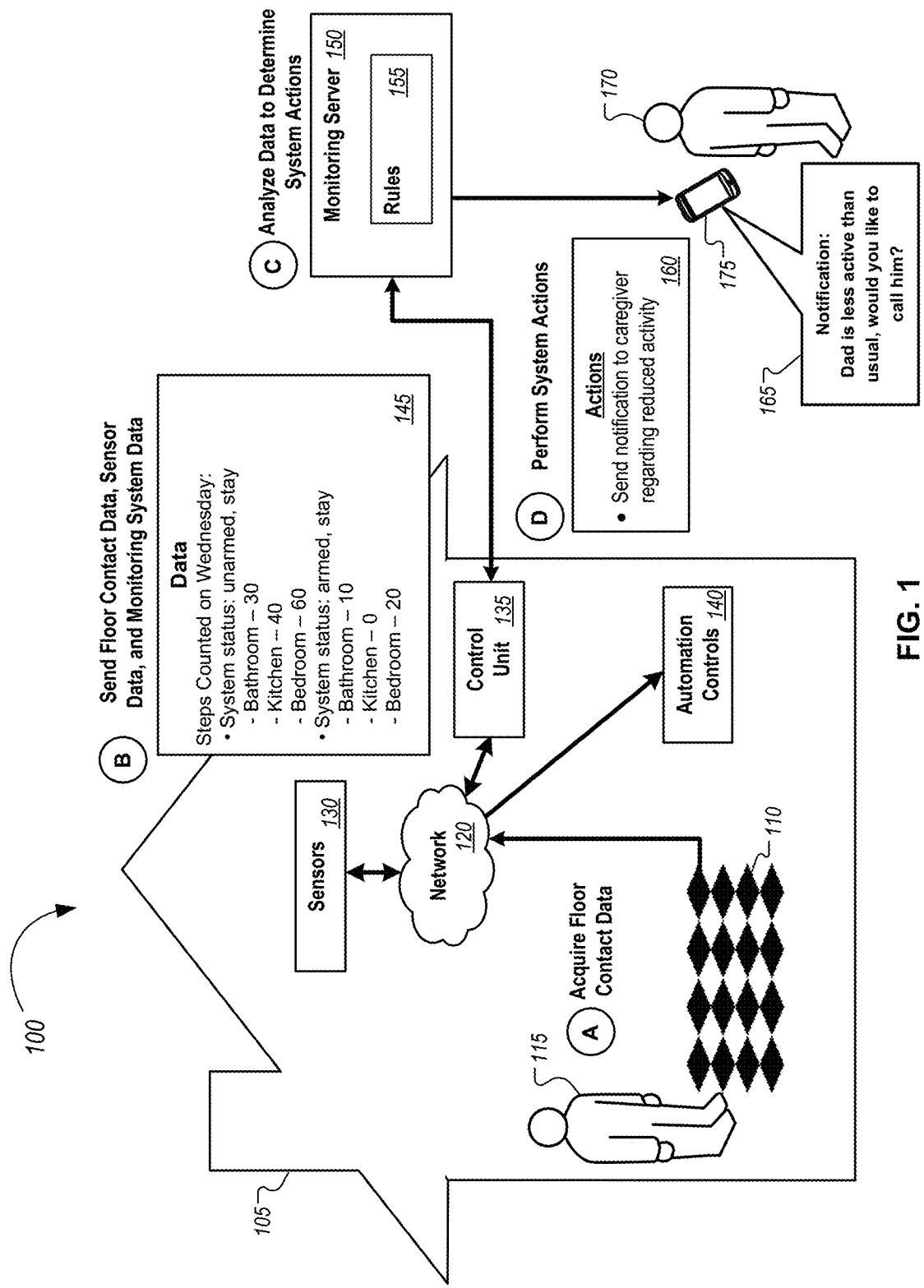
FIG. 1 is a diagram illustrating an example of a system for residential property control and configuration based on floor contact monitoring.

Many residents and homeowners equip their properties with monitoring systems to enhance the security, safety, or convenience of their properties. The property monitoring systems can include floor contact sensors, which provide data related to the contact of people, pets, and objects with floors within the property. For example, floor contact sensors located in a room of the property can collect data that can be processed to determine the number of people in the room. Floor contact sensors can also detect and identify various activities such as walking, running, jumping, or falling. By processing floor contact data over time, a monitoring system can identify trends in movement and activity within a property. When an anomaly occurs, such as someone falling on a floor or failing to get out of bed, the monitoring system can detect the anomaly and perform an action in response to the anomaly.

In some implementations, monitoring systems can dynamically control and configure devices and components of a property based on floor contact sensor data. For example, the monitoring system can use the data provided by the floor contact sensor to adjust the lighting or temperature within certain areas of the property, to adjust the status of the monitoring system, or to turn on or off appliances based on the location and activities of residents.

In some implementations, monitoring systems can improve accuracy of video analytics and machine vision using data provided by the floor contact sensor. For example, monitoring systems can filter video events based on floor contact sensor data in order to reduce a number of false alarms and to reduce the amount of unneeded camera data that is recorded and stored. Floor contact sensor data can also be used to trigger recording and/or storing camera data.

In some implementations, monitoring systems can correlate video analysis results with floor contact sensor data in order to improve accuracy of object detection. For example, based on floor contact sensor data, monitoring systems can determine a likelihood that detected objects were accurately detected and identified through video analysis. Additionally, monitoring systems can use floor contact sensor data can to identify individual objects such as people, animals, and inanimate objects. Identification of individual objects can be performed based on floor contact sensor data alone, or in conjunction with additional sensor data such as camera data.

Certain implementations of the disclosed systems, techniques, and process have particular advantages. In some cases, by analyzing floor contact monitoring data, a monitoring system can detect unexpected or undesired activity at a property and perform actions to mitigate or prevent furtherance of the activity. For example, certain properties may have occupancy limits. Based on floor contact monitoring data, the monitoring system can detect if there are too many people on the property, and can notify the property owner of the high occupancy.

In some cases, the monitoring system may be able to improve the efficiency or operation of the appliances of a property based on floor contact monitoring data. For example, the monitoring system can be programmed to control the HVAC system by turning on the heat only in occupied rooms of a property, and turning off the heat when a room is unoccupied.

In some cases, the monitoring system can process floor contact monitoring data to improve the convenience and comfort of a resident of the property. For example, the system can be programmed to turn on the coffee machine when a resident steps into the kitchen in the morning, or can turn on the shower faucet when a resident stands in front of the shower.

An advantage of property control and configuration based on floor contact monitoring is that it is not intrusive. Surveillance cameras can be used to track a resident's locations and activities within a property. However, cameras can be seen as violating a resident's privacy. Additionally, there are certain property areas where cameras are generally not desired, such as bathrooms. In these areas, floor contact monitoring can be used to monitor for accidental falls or slips, while still allowing for privacy.

Another advantage of property control and configuration based on floor contact monitoring is that it does not require operator action. There are many devices in which a person can contact authorities or caregivers if they fall or need assistance. However, studies show that many of the elderly or ill do not activate these devices because they are physically unable to (e.g., they are out of reach of the device). Additionally, some elderly or ill people may be too proud to activate the device, and/or they do not want to draw attention and concern. By performing analytics on data gathered by the floor monitor, once a fall is detected, the monitoring system can generate automatic alerts to the authorities or a caregiver. By learning insights about the day-to-day movement of the resident, the floor contact sensor is able to identify unusual activity and take needed action.

An additional advantage of property control and configuration based on floor contact monitoring is that it can prevent accidents, instead of responding to accidents after they happen. For example, if a resident of a home is limping, or walking more slowly than usual, the resident may not notice these changes in his or herself. The monitoring system can detect the change based on analyzing floor contact data trends over time. The monitoring can notify a caregiver of the change in behavior before an accident occurs, so that the caregiver can check on the resident or take the resident to a see a doctor. This may prevent the resident from having an accident in the home.

The details of one or more implementations of the subject matter described in this specification are set forth in the accompanying drawings and the description below. Other features, aspects, and advantages of the subject matter will become apparent from the description and the drawings.

FIG. 1 is a diagram illustrating an example of a system 100 for property control and configuration based on floor contact monitoring.

The property 105 is monitored by a property monitoring system. The property 105 can be a home, another residence, a place of business, a public space, or another facility that has a floor contact sensor 110 installed and is monitored by a property monitoring system. The monitoring system includes one or more sensors 130 located at the property 105 that collect sensor data related to the property 105. In the example of FIG. 1, the resident 115 lives alone. The resident has a caregiver 170 who may live in another home. The property monitoring system has the ability to notify the resident 115 and/or caregiver 170 of various anomalies and statuses of the property 105. The property monitoring system also has the ability to communicate with and control various devices on the property 105.

In stage (A) of FIG. 1, the floor contact sensor 110 collects floor contact data. The floor contact sensor 110 can be attached to any type of flooring such as a carpet, tile, or wood floor. The floor contact sensor 110 can also be incorporated into a mat, e.g., a kitchen mat, bath mat, outdoor mat, or garage mat. The floor contact sensor 110 can collect data related to the resident 115's activities based on sensing contact with the floor. For example, the floor contact sensor 110 can detect the pressure of the resident 115's feet on the floor.

In some examples, the floor contact sensor 110 can use pressure sensors to detect movement and weight distribution. Pressure sensors can include, for example, strain gauges. A strain gauge is a sensor that can output an electrical resistance that varies with applied force. Thus, a strain gauge can convert force, pressure, weight, etc., into a change in electrical resistance.

When used on tiled floors, the pressure sensors of the floor contact sensor 110 can be built into individual tiles. The tiles can be installed and grouted as normal for floor tiles. An example tile can have four layers. The first layer is a substrate for adhesion to the subfloor. The second layer is embedded with logic systems and/or interconnect systems. The third layer can vary in resistance or charge based on pressure or strain.

The third layer also can have mechanical structures to support transmission of force from the surface of the tile. The fourth layer can include a number of cosmetic and protective layers, similar to the surface of an ordinary floor tile. The floor contact sensor 110 can function when the tiles are covered by rugs, or when dirty or wet.

The tiles can be any type or size of tile. For example, the tiles can be ceramic, porcelain, stone, glass, marble, granite, metal, clay, cement, or slate. The tiles can also be any type of synthetic tile such as vinyl or laminate. Larger tiles can contain many individual sensors, while smaller tiles may only contain one sensor.

Each tile can be individually capable of measuring the force applied to it from a person or object. In some applications, the tile might be broken into multiple divisions, as in a sheet of mosaic tiles, each capable of measuring an independent force reading corresponding to its surface area. Each tile can be interchangeable with any other.

Instead of or in addition to pressure sensors, the floor contact sensor 110 can include fiber optics on the surface of a tile. The outline of an object, such as a foot, can be determined based on the fiber optic sensors that are blocked from light.

Instead of or in addition to pressure sensors, the floor contact sensor 110 can include capacitive sensors incorporated into a tile. As a person walks across the tile or otherwise contacts the tile, the capacitive sensors can detect and measure changes to the local electric field caused by the presence of the person. In this way, the capacitive sensors can detect the presence of an object, e.g., the person, as well as direction and velocity of motion of the object.

When a floor contact sensor 110 is used on a carpeted floor, the pressure sensors can be built into a carpet pad that lies underneath a carpet. Each segment of carpet pad or underlayment can be individually capable of measuring the force applied to it from a person or object. The size and separation of sensors can vary. Smaller sensors placed close together result in higher levels of sensitivity and better resolution.

Small sensors with high resolution can be sensitive enough to distinguish between different residents 115 in a household based on various factors such as their weights, footstep sizes, and walking gaits. The floor contact sensor 110 can also measure the number of points of contact with the floor. For example, a crawling baby or a pet will have four points of contact, a person who walks with a cane will have three, and a person walking will have two.

To account for other furniture in a room with a floor contact sensor 110, a "base" state can be established. The base state can be a state of the floor contact sensor 110 in the absence of human presence and/or activity. The base state can be established when the floor contact sensor 110 is initially installed, when new residents move in, and any time furniture is moved. To establish the base state, a user, e.g., an installer or resident, can install the floor contact sensor 110 and arrange furniture on the floor. The user then can step out of the room and verify that no other item, person, or pet is in the room that usually would not be there. The user can then access the monitoring system control unit 135 select that the floor contact sensor 110 is in its base state. This base state allows for the floor contact sensor 110 to recognize furniture and other inanimate objects that are normally in the room so that it can recognize other pressure points that are relevant to the resident. The weight from the normal objects in the room no longer register for the floor contact sensor 110. This is similar to setting a scale to "zero" as a reference point before stepping onto the scale.

After installation, the monitoring system can undergo a training phase, where the monitoring system uses machine learning to identify the residents 115 of the property and their routines. The monitoring system can learn the weights and points of contact indicative of particular pets, children, and adults on the property. When a new object is added to a room with a floor contact sensor 110, the user can input the new object into the monitoring system through an interface with the control unit. Alternatively, the monitoring system can prompt the user to identify the new object through the control unit or other means.

Other settings can be adjusted by the resident 115 or caregiver 170 based on individual circumstances. For example, if the resident uses a cane, walker, or wheelchair, the monitoring system can be configured to recognize the pattern of movement when the resident 115 uses the equipment. This allows the floor contact sensor 110 to detect when a resident 115 is using the equipment, and when the resident is not using the equipment.

There can be different levels of sensitivity for the floor contact sensor 110. For example, if there is a higher percentage for an incident to occur in one area of the property compared to other areas, such as the hallway versus the bedroom, the sensitivity for the floor contact sensor 110 in those more accident-prone areas can be adjusted accordingly by the installer, resident, or caregiver. If the resident 115 has a pet, especially a heavier pet, the resident may set the sensitivity of the floor contact sensor 110 to a lower state so that the floor contact sensor 110 only registers the activity of humans.

When installing the floor contact sensor 110, a map of the property and location of the floor contact sensors can be created. For example, the floor contact sensor 110 might only be installed in certain areas of the home. The map of the property can be stored on the monitoring server 150. Over time, the monitoring system can use machine learning to improve the map of the property. For example, a floor contact sensor 110 may be installed in an upstairs hallway, and a downstairs living room, but not on the stairs in between. The monitoring system can learn over time that a resident typically takes 15 seconds to walk up or down the stairs, based on the time between stepping off of one floor contact sensor 110 and stepping on to the other. If the floor contact sensor 110 detects the resident stepping from the upstairs hallway toward the stairs, and then after 15 seconds does not detect the resident's footsteps in the downstairs living room, the monitoring system can recognize the anomaly and determine that the resident may have fallen on the stairs.

When incorporated into portable mats, floor contact sensors can be positioned and repositioned by the resident 115. The resident 115 can position the portable mats in locations of interest to the resident 115. For example, the resident 115 can position a portable mat inside a front door, outside a front door, in a garage, near a child's bed, etc. When the resident 115 positions or repositions a particular portable mat, the resident can input the new position of the particular portable mat to the monitoring server 150, e.g., through a user interface provided through an application presented on an electronic device. The monitoring server 150 can integrate the positions of the portable mats into the map of the property. Over time, as described above, the monitoring system can use a machine learning process to improve or adjust the map of the property.

The floor contact sensor 110 sends the floor data to the control unit 135 through the network 120. There are multiple means by which the pressure sensors within the floor contact sensor 110 can be transmitted to the control unit 135. For a tile floor, the edges of the tiles can have electrical contacts that connect to the adjacent tiles in each row or column. The contacts can interlock in the same way that plastic floor tiles have tabs on two edges and receptacles on the other two edges. The tiles can include as many contacts as necessary to carry electric power to the pressure sensors and to transmit data signals from the pressure sensors.

In some implementations, the passive sensor elements of each tile can be wired together by row and column, in series, or parallel, such that an active circuit wired to the edge receives an accumulation of readings from that row or column. The connections or sensors at each tile may incorporate some redundancy depending on the exact implementation to allow readout along both the row and the column.

In some implementations, an active controller in each tile can be uniquely addressable by row and column. The contacts can provide power for this controller as well as a data conduit.

In some implementations, each tile controller can use a wireless data connection to the property monitoring system. The connectors can be used to distribute power to the sensors and wireless transmitter. The hardwired connection can also be used to determine the position of each tile in an array. The position of each tile can be determined either via analog measurement of signal across the power lines to determine the relative position in the row or column, or by exchanging addresses or identification with neighboring tiles.

In some implementations, the tiles can be completely wireless. Power can be provided by an inductive mat installed beneath the tiles, or by wireless signals such as radio frequency signals. For any wireless data or power process, additional layers of tile may be added to provide antennae adjacent to the tops or bottoms of the tiles.

A floor contact sensor 110 can be integrated into a carpet pad or underlayment for wood flooring. In this implementation, the orientations and connections are similar to those for tiles. In a carpet pad or underlayment, the pressure sensors can connect to one another through connections internal to the pad.

Other sensors 130 of the monitoring system collect various sensor data from the property 105. For example, 130 the sensors can include thermometers, cameras, microphones, appliance monitors, and water flow meters. Data from sensors 130 can be correlated with floor contact sensor 110 data to assess the activity of a resident and detect any anomalies.

For example, a resident may wake most days at 8:00 am, walk to the bathroom, use three gallons of water, walk to the kitchen, turn on the lights, coffee maker, toaster, and radio, then sit in a kitchen chair. The floor contact sensor 110 can detect the resident 115's activities such as getting out of bed, walking to the bathroom, walking to the kitchen, and sitting in the chair. The water flow meter can detect the water usage in the bathroom. The appliance monitors can detect the power flowing to the lights, toaster, and radio. Microphones can collect audio from the resident's activities around the property, and the monitoring system can determine that the audio represents the sounds of flowing water in the bathroom, and of the radio in the kitchen. Cameras can collect visual imagery of various areas of the property, and the monitoring system can determine that the visual imagery represents images of a resident moving throughout the property.

The sensors 130 send the sensor data to the control unit 135 through the network 120. The control unit 135 receives data from the floor contact sensor 110, and the sensor data from the sensors 130. The control unit 135 can be, for example, a computer system or other electronic device configured to communicate with the floor contact sensor 110 and sensors 130. The control unit 135 can also perform various management tasks and functions for the monitoring system. In some implementations, the resident 115 of the property, a caregiver 170, or another user, can communicate with the control unit 135 (e.g., input data, view settings, or adjust parameters) through a physical connection, such as a touch screen or keypad, through a voice interface, or over a network connection.

The floor contact sensor 110 and sensors 130 may communicate with the control unit 135 through a network 120. The network 120 can be any communication infrastructure that supports the electronic exchange of data between the control unit 135, the floor contact sensor 110, and sensors 130. For example, the network 120 may include a local area network (LAN). The network 120 may be any one or combination of wireless or wired networks and may include any one or more of Ethernet, Bluetooth, Bluetooth LE, Z-wave, Zigbee, or Wi-Fi technologies.

In stage (B) of FIG. 1, the control unit 135 sends the various data 145 to a remote monitoring server 150, where the data 145 can include the data from the floor contact sensor 110, and sensor data from the sensors 130. The control unit 135 also sends the configuration of the system to the monitoring server 150, indicating whether the system is armed or disarmed.

The monitoring server 150 may be, for example, one or more computer systems, server systems, or other computing devices that are located remotely from the property 105 and that are configured to process information related to the monitoring system at the property 105. In some implementations, the monitoring server 150 is a cloud computing platform.

The control unit 135 communicates with the monitoring server 150 via a long-range data link. The long-range data link can include any combination of wired and wireless data networks. For example, the control unit 135 can exchange information with the monitoring server 150 through a wide-area-network (WAN), a broadband internet connection, a cellular telephony network, a wireless data network, a cable connection, a digital subscriber line (DSL), a satellite connection, or other electronic means for data transmission. The control unit 135 and the monitoring server 150 may exchange information using any one or more of various communication synchronous or asynchronous protocols, including the 802.11 family of protocols, TCP/IP, GSM, 3G, 4G, 5G, LTE, CDMA-based data exchange or other techniques. In some implementations, the long-range data link between the control unit 135 and the monitoring server 150 is a secure data link (e.g., a virtual private network) such that the data exchanged between the control unit 135 and the server 150 is encoded to protect against interception by an adverse third party.

In some implementations, various other monitoring system components located at the property 105 communicate directly with the monitoring server 150 (e.g., sending data directly to the monitoring server 150 rather than sending data to the server 150 via the control unit 135). For example, the floor contact sensor 110, the sensors 130, the automation controls 140, or other devices at the property 105 can provide some or all of the data 145 to the monitoring server 150, e.g., through an internet connection.

In some implementations, the control unit 135 processes some or all of the data 145 before sending the data 145 to the monitoring server 150. For example, the control unit 135 may compress or encode the data 145 to reduce the bandwidth required to support data transmission. The control unit 135 can also aggregate, filter, transform, or otherwise process some or all of the data 145.

In the example of FIG. 1, the data 145 includes floor contact sensor 110 data. The data 145 collected from the floor contact sensor 110 includes the number of footsteps that the resident 115 took on a single day. The data 145 includes the number of footsteps in each room of the property 105 that has a floor contact sensor 110. The data includes the number of footsteps taken while the monitoring system was armed, and the number of footsteps taken while the monitoring system was unarmed. The data 145 may also include data from sensors 130 at the property, such as temperature data, camera data, microphone data, appliance monitor data, and water flow meter data.

In stage (C), the monitoring server 150 analyzes the data 145 received from the control unit 135. For example, the monitoring server 150 can analyze the floor contact sensor 110 data to compare the current activity level of the resident 115 to previous activity levels. The monitoring server 150 can track and compare data over any time period such as days, weeks, or months. The monitoring server 150 can detect trends, such as gradually decreasing activity over time, and anomalies, such as a rapid decrease in activity.

The monitoring server 150 can also detect anomalies in the health or well-being of the resident 115. For example, the floor contact sensor 110 can indicate if a resident 115 has fallen or is lying on the floor. The floor contact sensor 110 can also monitor the resident 115's gait. A resident 115 may typically walk at a certain speed, with a certain amount of weight on each foot. If the resident 115's gait slows down over time, or if the resident 115 starts to limp, the monitoring server 150 can detect this change. If the resident 115 typically uses a cane when walking, the monitoring server 150 can detect an anomaly if the resident 115 walks without the cane. Similarly, if the resident 115 rarely uses a cane, e.g., when the resident 115 feels unstable, the monitoring server can detect an anomaly if the resident 115 increases their use of the cane.

The monitoring server 150 can use a rules-based system 155 to determine system actions 160. The rules 155 can be default rules, set in advance by a system administrator. The rules 155 can also be custom rules, set or modified by the resident 115 or another authorized user of the monitoring system. The rules 155 may be general, such that they are applied to more than one property, or they may be specific to the particular property 105. In some implementations, the rules 155 can be customized according to a particular room, the time of day, or other factors.

An example rule 155 may state that an activity decrease of 20 percent or more over 24 hours warrants a notification 165 to a caregiver 170. In the example of FIG. 1, the monitoring server 150 evaluates the data 145 and determines that the resident 115's activity has decreased by 25 percent over the past 24 hours. Thus, the monitoring server 150 determines the action 160 of notifying the caregiver 170.

Other rules 155 can be related to a resident 115's routine. For example, the floor contact sensor 110 can detect when a resident 115 steps on the bedroom floor in the morning. Based on floor contact sensor 110 data, the monitoring server 150 may determine that the resident 115 typically steps on the bedroom floor between 7:30 am and 8:00 am. A rule 155 may state that if the floor contact sensor 110 does not detect the resident 115 stepping on the bedroom floor by 9:00 am, the monitoring system will perform an action 160, e.g., the monitoring system will notify the caregiver 170.

In another example, the monitoring server 150 can determine, based on floor contact sensor 110 data, the length of time that a resident 115 is in a certain room of the property, such as a bathroom. The monitoring server 150 can determine the length of time that a resident 115 is in a certain room of a property based on data from a floor contact sensor 110 in that room, a floor contact sensor 110 in an adjacent room, or both. For example, if a resident steps from a bedroom with a floor contact sensor 110 into a bathroom without a floor contact sensor 110, the monitoring server can determine, based on the resident's footstep path, that the resident 115 has entered the bathroom.

Based on floor contact sensor 110 data, the monitoring server may determine that the average time that the resident 115 spends in the bathroom is 10 minutes. A rule 155 may state that if the resident 115 spends more than 20 minutes in the bathroom, the monitoring system will perform an action 160, e.g., the monitoring system will notify the caregiver 170. An exception to this rule could be that the monitoring system will not take an action 160 if the resident 115 turns on the shower, as determined by the monitoring server's 150 analysis of water flow meter data.

The rules 155 can vary depending on the status of the monitoring system. For example, a monitoring system may have settings of "unarmed, stay," "armed, stay," and "armed, away." If the resident 115 has a caregiver, the monitoring system may have additional settings that indicate if the resident is home alone, or home with a caregiver. For example, when the resident 115 is at the property alone, the resident 115 may set the monitoring system to a status such as "armed, stay, alone." When the monitoring system status is set to "armed, stay, alone," a rule 155 may be that if the floor contact sensor 110 detects a fall, the monitoring system performs the action 160 of notifying emergency personnel.

When the resident 115 is at the property with a caregiver 170, the resident 115 may set the monitoring system to a status such as "armed, stay, accompanied." When the monitoring system status is set to "armed, stay, accompanied," a rule 155 may be that if the floor contact sensor 110 detects a fall, the monitoring system requests confirmation from the caregiver 170 or the resident 115 before taking the action 160 of notifying emergency personnel.

In some implementations, the resident 115 or the caregiver 170 can customize the one or more rules 155 according to their preferences. In some implementations, the resident 115 or caregiver 170 can set the one or more rules 155 through a software application executing on their mobile devices, through a graphical interface provided by a browser or application on a computing device, and/or through interacting with a physical interface of the control unit 135 of the property monitoring system.

The server 150 can determine any of various actions 160 in response to analyzing the data 145. For example, the server 150 may determine actions 160 that include sending a notification 165 to a mobile device 175, sending an instruction to the automation controls 140 to adjust a setting at the property 105, sending a command to a sensor 130 to collect and send additional sensor data, sounding an alarm of the property 105, or sending an alert to a third-party, such as security personnel or emergency services.

In stage (D), the server 150 performs the system actions 160. For example, the server 150 can perform the actions 160 by sending a command to a device of the monitoring system through a signal to the control unit 135 over the long-range data link. In some implementations, the server 150 can send a notification 165 and/or alert to the mobile device 175 of the caregiver 170. The server 150 can communicate with the mobile device 175 through a cellular telephony or wireless data network, through a WAN or LAN, through Wi-Fi, or through another wired or wireless communication link.

In the example of FIG. 1, the monitoring server 150 performs the action 160 of sending a notification 165 to the mobile device 175 of the caregiver 170. The notification 165 informs the caregiver 170 that the resident 115 is less active than usual, based on the reduction of steps over the course of 24 hours. The notification 165 prompts the caregiver 170 to call the resident 115.

In some implementations, the actions 160 may include sending a notification 165 to the mobile device 175 of the caregiver 170 and requesting a response from the caregiver 170. For example, the monitoring server 150 can send a message requesting permission to call emergency responders, activate an automated system at the property 105, and/or call the resident 115.

Daily activity can be recorded and integrated into the property monitoring system. The monitoring system can generate reports to tell the resident and caregiver whether the floor contact sensor 110 detects low, medium, or above average activity.

The floor contact sensor 110 can add to other information collected by the monitoring system to create "smart schedules." The floor contact sensor 110 can send different notifications 165 to incentivize the customer to "move more" or be more active for the day. An example of how the floor contact sensor 110 could interact with smart schedules could be if every day at 8:00 am the resident rises out of bed and walks on a floor that includes a floor contact sensor 110 to the bathroom. The smart schedule will know to expect this behavior, and turn on lights downstairs, adjust the temperature in the property now that the resident 115 is awake, etc. However, if the resident deviates from the usual schedule, and the floor contact sensor 110 does not register movement at 8:00 am, then a caregiver may be notified.

The floor contact sensor 110 can collect data on other patterns. For example, if the floor contact sensor 110 learns that when the resident 115 uses the bathroom in the middle of the night, she is in there for an average of 5 minutes by tracking footsteps to and from the bathroom. However, if the resident 115 is in the bathroom for more than the average 5 min, it could mean that the resident 115 has fallen in the bathroom and the proper avenues of alerts could be taken.

The control unit 135 can activate one or more property automation controls 140, possibly through the network 120. The property automation controls 140 connect to one or more devices of the property 105 and enable control of various property actions 160. For example, the property automation controls 140 can adjust a thermostat, turn on or off lights, turn on or off cameras, turn on or off faucets and showers, and turn on or off a radio or television.

In some implementations, the data from the floor contact sensor 110 can trigger other sensors to turn on or off. For example, a resident 115 may not want cameras and microphones to be turned on all of the time. However, a resident 115 may allow cameras and microphones that only turn on in certain events. For example, if, on a given morning, the floor contact sensor 110 detects the resident 115 entering the kitchen but then does not detect power to any kitchen equipment or appliances, the monitoring system can activate a camera in the kitchen so that the caregiver 170 can look at the camera footage to determine if there has been an accident.

Cameras or microphones may also turn off, or remain off, in response to certain events detected by the floor contact sensor 110. For example, if the floor contact sensor 110 detects a person walking through the property, and the monitoring system determines, based on the detected weight, footstep size, and gait, that the person is the resident 115, the monitoring system may turn off the cameras and microphones. If the floor contact sensor 110 detects a person walking through the property, and the monitoring system determines, based on the detected weight, footstep size, and gait, that the person is not the resident 115 or other known household member, the monitoring system can continue to record, or begin to record, using cameras and microphones. In this way, the floor contact sensor 110 can improve security by triggering surveillance cameras and microphones when the floor contact sensor 110 detects and unknown person, while still maintaining privacy for the resident 115.

Another action 160 that the monitoring system could take is to activate a "personal assistant" electronic device. The personal assistant can ask the resident 115 a verbal question, such as "is everything alright?" If the resident 115 does not respond, or if the resident 115 responds negatively, the monitoring system can then notify a caregiver 170 or emergency personnel.

An example of automation controls 140 could be an automatic drain in a bathtub. If contact-sensitive tiles are installed in a bathtub, they can detect if a resident 115 falls in the bathtub. The monitoring system can then take the action 160 of notifying emergency personnel while also activating the automatic bathtub drain.

Another application of the floor contact sensor 110 is to perform an occupancy check in the property 105. If a resident 115 is concerned about whether there is an intruder in the home, the resident 115 can check the monitoring system to see if there are any people detected walking through the property. The floor contact sensor 110, integrated with motion sensors, surveillance cameras, and door and window sensor, can keep the resident 115 informed if there are any intruders, and can be programmed to automatically notify emergency personnel in the event of intrusion.

An application that can be used with elderly or ill individuals is to assist with confusion of daily schedules. A resident 115 may become confused on whether it is daytime or nighttime and try to exit the property 105 at night. If the floor contact sensor 110 detects that an elderly or ill resident 115 is approaching the front door at night, the monitoring system can proactively lock the front door, turn on video cameras, and send a caretaker 170 a notification 165 about possible confusion on behalf of the resident 115. With the floor contact sensor 110, there is an extra level of protection against confusion by proactively sending alerts before the resident 115 leaves the property 105.

In some examples, the floor contact sensor 110 can also be used in conjunction with a door contact sensor to determine a direction from which a door was opened or closed. For example, a door contact sensor can determine when a door opens and when a door closes. The floor contact sensor 110 can be positioned inside the door, outside the door, or both. When a person exits, a sequence of sensor data may include the floor contact sensor 110 detecting weight inside the door, the door contact sensor detecting the door opening, the floor contact sensor 110 detecting weight outside the door, and the door closing. Based on the sequence of sensor data, the monitoring system can determine that a person exited through the door. A similar process can be used to determine when a person enters through the door.

In some examples, the monitoring system can use floor contact sensor data to trigger a camera, e.g., a surveillance camera, a doorbell camera, etc., to record and/or store camera data. For example, the floor contact sensor 110 can be integrated into a doormat and placed outside of a door to a property, e.g., on a front porch. The floor contact sensor 110 may detect a person standing on the doormat and can send collected floor contact sensor data to the monitoring server. The monitoring server can then send a command to a doorbell camera to capture images of the front porch.

In some examples, the monitoring system can use floor contact sensor data to verify video analysis of camera images, to detect video analysis inaccuracies, or both. For example, a doorbell camera may capture images of a person standing on a front porch, while the floor contact sensor 110 detects the weight of the person standing on the doormat. The monitoring system may perform video analysis, e.g., facial recognition, on the camera images. Based on facial recognition, the monitoring system may determine that the person is a particular resident of the property. The monitoring system can verify the identity by referencing a stored weight of the particular resident and comparing the stored weight to the detected weight. If the stored weight and the detected weight vary by more than a threshold amount, the monitoring system may determine that the video analysis is inaccurate.

In some examples, the monitoring system can determine a likelihood of certain occurrences based on floor contact sensor data, alone or in conjunction with other sensor data. For example, based on floor contact sensor data indicating a weight of a detected person and based on stored weight data for residents of a property, the monitoring system can determine a likelihood that the detected person is a resident of the property.

In some examples, the monitoring system can use floor contact sensor data to augment determinations based on other sensor data. For example, the monitoring system may perform video analysis on camera images captured in poor lighting conditions and/or in conditions that obscure the camera images, e.g., in rainy conditions. Based on facial recognition, the monitoring system may determine a likelihood that the person is a particular resident of the property. The monitoring system can augment the facial recognition analysis using the floor contact sensor data by referencing a stored weight of the particular resident of the property. If the stored weight and the detected weight match within a threshold deviation, the monitoring system can determine an increased likelihood that the detected person is the particular resident.

The floor contact sensor 110 can be used in properties where there are multiple people, as well as pets. Through machine learning, the floor contact sensor 110 can learn the daily, weekly, and monthly patterns of movement of individuals in the household. The floor contact sensor 110 can create profiles of individuals in a household based on each individual's weight, walking gait, and activities. For example, the floor contact sensor 110 can identify children based on their lesser weight, small footsteps, and heavy, quick footsteps.

In some examples, the resident 115 can configure the monitoring system to detect certain activities. In some examples, the resident 115 can place a portable floor mat that includes a floor contact sensor 110 in a particular location for detecting certain activities. For example, the resident 115 can place the portable floor mat near a child's bed in order to detect the child getting out of bed at night. In another example, the resident 115 can place the portable floor mat near a refrigerator in order to detect people approaching the refrigerator.

In another example, the resident 115 can place a mat that includes a floor contact sensor 110 near or under a pet food dish. The floor contact sensor 110 can detect a weight of pet food remaining in the dish. The floor contact sensor 110 can also detect weight of a pet standing on the mat. Based on the floor contact sensor data, the monitoring system can determine times, frequencies, durations, and quantities of pet food consumption. The floor contact sensor can also collect data indicating the weight of the pet.

Based on the floor contact sensor data, the monitoring system can identify anomalies in pet behavior, e.g., if the frequency at which the pet approaches the food bowl decreases or increases. The monitoring system can also identify the weight of food in the food bowl. Based on the floor contact sensor data, the monitoring system can generate alerts for the resident 115. For example, the monitoring system can generate an alert to the user indicating that the food bowl is empty. In some examples, based on the floor contact sensor, the monitoring system can control an automatic pet feeder in order to release food or to stop releasing food.

In some examples, based on the floor contact sensor data, the monitoring system can determine if pet food is consumed by a pet other than the intended pet. For example, the portable floor mat including the floor contact sensor can be placed near a food dish containing food intended for a fifteen-pound pet. The resident can input a setting to the monitoring system indicating that the weight of the intended pet is fifteen pounds. The monitoring system can then detect if a weight of a pet consuming the food differs from the set weight by an amount greater than a deviation, e.g. plus or minus ten percent. Thus, if a pet weighting fifty pounds approaches the food bowl, steps on the floor mat, and consumes the food, the monitoring system can determine that the weight of the pet exceeds the set weight by more than ten percent. The monitoring system can also determine that the weight of the food decreases due to the fifty-pound pet consuming the food. The monitoring system can then generate a notification to the resident 115 indicating that the food was consumed by a pet other than the intended pet.

Although the example in FIG. 1 is of a floor contact monitoring application, contact sensors can be integrated into tiles used for applications other than floors. For example, contact-sensitive tiles can be used on a countertop, backsplash, wall, shower floor, sink, or bathtub. The connections, functions, and integration of contact-sensitive tiles in these applications are the same as for floor contact monitoring tiles.

In a countertop example, contact-sensitive tiles can be used to detect an impact, such as if a resident 115 falls and hits his or her head on a counter. Additionally, if countertop tiles detect a resident 115 frequently leaning on the countertop for support, it may be an indication that the resident 115 needs assistance with walking.

In a sink, contact-sensitive tiles can be used to detect items placed in the sink. For example, the monitoring system can detect the presence of dishes or other items when they are placed in the sink, based on increased weight detected by the contact-sensitive tiles. The monitoring system can then determine a length of time passed since dishes were added to the sink.

In a property such as a rental property, in response to the monitoring system detecting dishes in the sink, the monitoring system can generate a notification to the property owner. For example, the monitoring system can send a notification to the property owner indicating that dishes have been left in the sink for more than a threshold period of time, e.g., twenty-four hours. In this way, the property owner can receive an indication of the cleanliness of the rental property.

In a bathtub or hot tub, the tiles can be used to detect if a resident 115 has been in the bathtub too long, or if a person in the bathtub is remaining completely still for a period of time. This could indicate that the person is unconscious, and could trigger the system to notify emergency personnel. Contact-sensitive tiles in a bathtub can be calibrated to account for water in the bathtub.

Contact-sensitive tiles in a bathtub can be calibrated using a similar process as can be used to calibrate the floor contact sensor 110 of a room. To account for water in a bathtub with contact-sensitive tiles, a "base" state can be established. The base state can be established, for example, when the contact-sensitive tiles are initially installed, or when new residents move in. To establish the base state, a user, e.g., an installer or resident, can install the contact-sensitive tiles and fill the bathtub with an amount of water that could be used for a bath. The user can then access the monitoring system control unit 135 and select that the bathtub in its base state. This base state allows for the contact-sensitive tiles to recognize water in the bathtub. The weight from the water in the bathtub no longer registers for the contact-sensitive tiles. This is similar to setting a scale to "zero" as a reference point before stepping onto it.

Once the contact-sensitive tiles in the bathtub are calibrated, the monitoring system can detect the presence of the resident 115 when the resident 115 enters the bathtub. For example, the monitoring system can determine that the resident 115 is in the bathtub based on increased weight detected by the contact-sensitive tiles. The monitoring system can also determine the presence of the resident 115 in the bathtub based on the distribution of weight in the bathtub. For example, contact-sensitive tiles in a bathtub full of only water may detect an even pressure throughout the surface of the bathtub. Once the resident 115 enters the bathtub, the detected pressure will be unevenly distributed between the contact-sensitive tiles. The monitoring system can determine that the resident 115 is in the bathtub based on the uneven distribution of the detected pressure.

In some examples, a floor contact sensor 110 can be installed or placed in a garage. The monitoring system can then detect and track vehicular movement based on changes in weight detected by the floor contact sensor 110. The floor contact sensor 110 can detect a vehicle entering, exiting, and parked in the garage. While a vehicle is parked in the garage, the floor contact sensor 110 can detect changes in a weight of the vehicle. Based on changes in weight, the monitoring system can determine when a person, or people, enter and exit the vehicle.

In some examples, based on a detected increase in weight of the vehicle, the monitoring system can determine an identity of the person entering the vehicle. For example, the monitoring system can reference stored weights for residents of the property to determine the identity of the person. In some examples, the monitoring system can determine if the increase in weight of the vehicle is due to an adult entering the vehicle or due to a child entering the vehicle. In response to detecting only a child entering the vehicle, the monitoring system can perform one or more actions, such as generating a notification for a resident of the property.

In some examples, based on a detected increase in weight of the vehicle, the monitoring system can send a command to one or more components or devices at the property. For example, in response to detecting a person entering the vehicle, the monitoring system can send a command to a garage door to open. In some examples, in response to detecting a person entering the vehicle, the monitoring system can send a command to one or more cameras to capture images, e.g., of the garage or areas near the garage.

Though described above as being performed by a particular component of system 100 (e.g., the control unit 135 or the monitoring server 150), any of the various control, processing, and analysis operations can be performed by either the control unit 135, the monitoring server 150, or another computer system of the system 100. For example, the control unit 135, the monitoring server 150, or another computer system can analyze the data from the floor contact sensor 110 and from the sensors 130 to determine the actions 160. Similarly, the control unit 135, the monitoring server 150, or another computer system can control the various sensors 130, the floor contact sensor 110, and/or the property automation controls 140 to collect data or control device operation.

Figure 2:
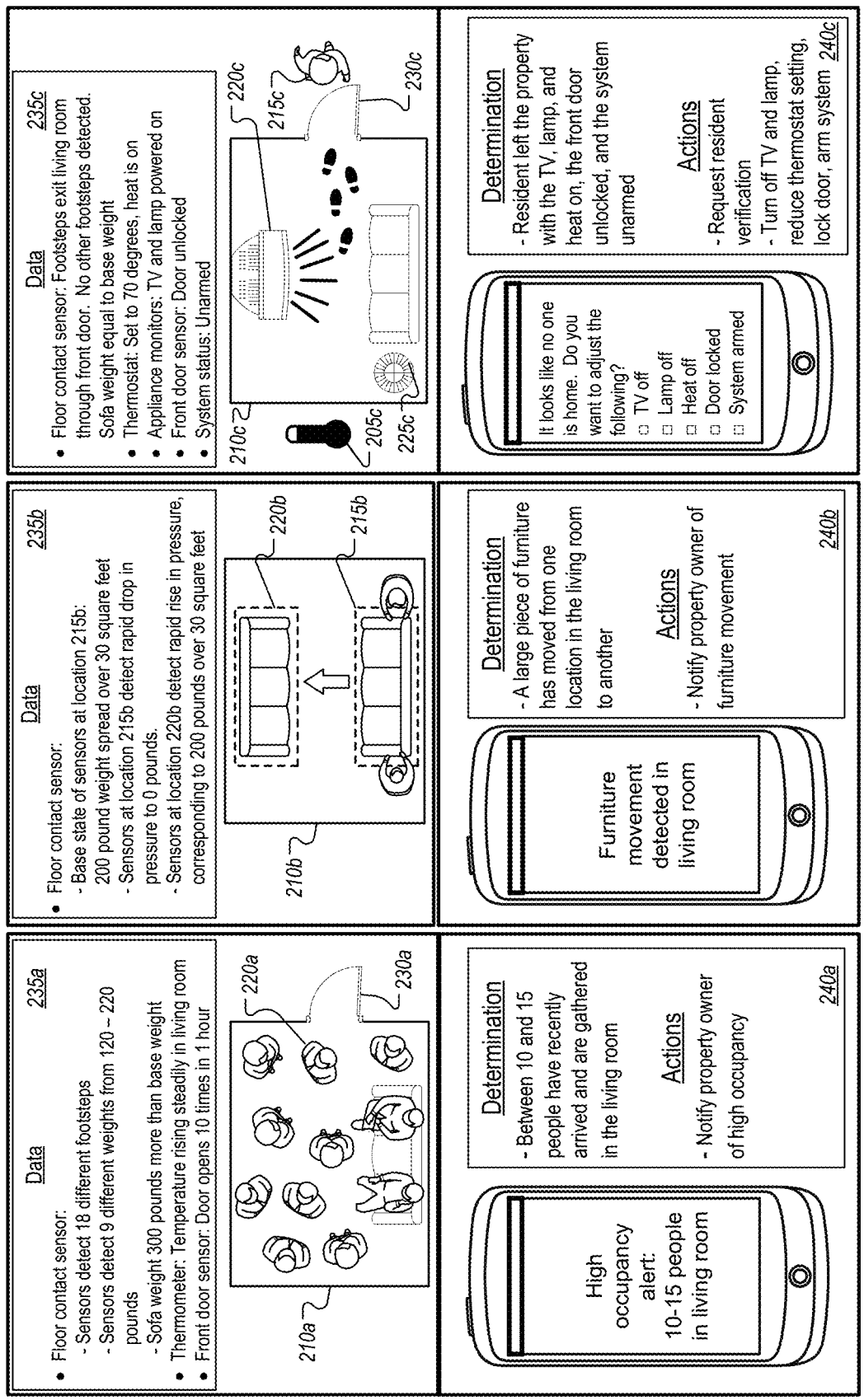
FIGS. 2A-2C are diagrams illustrating examples of rental property control and configuration based on floor contact monitoring.

FIG. 2A-2C are diagrams illustrating examples of rental property control and configuration based on floor contact monitoring.

In the example of FIG. 2A, a floor contact sensor 210a is installed in the living room of a rental property. The rental property can be, for example, a short-term vacation rental property, or a long-term leased property. To prevent noise and damage to the property that can be caused by large parties, the property owners may write the terms of the rental agreement limiting the number of people allowed in the property to six people.

The floor contact sensor 210a can be used to monitor the occupancy of the rental property. In the example of FIG. 2A, eleven people are gathered in the living room for a party. Nine guests 220a are standing on the floor, while two guests 220a are sitting on the sofa. The floor contact sensor detects the footsteps of the guests 220a who are standing. The floor contact sensor can detect the weight of the guests 220a, and the sizes of their footsteps. The data collected by the floor contact sensor can be used by the monitoring system to determine the approximate number of people standing in the living room.

The floor contact sensor detects eighteen footsteps. The monitoring system analyzes the floor contact sensor 210a data to determine the sizes of the eighteen footsteps. The monitoring system determines that the eighteen footsteps include footsteps that are nine different sizes, with two footsteps per size. Additionally, the monitoring server analyzes the floor contact sensor 210a data to determine that there are nine different detected objects on the floor, each weighing between 120 and 220 pounds.

The monitoring system analyzes the floor contact sensor 210a data and determines that the weight of the sofa is different from its base weight. The base weight of the sofa is 200 pounds. The sofa currently weighs 500 pounds, which is 300 pounds more than the base weight.

The monitoring system evaluates the data collected by the floor contact sensor 210a to estimate the number of guests 220a in the living room. Based on the nine different footstep sizes, and the nine detected objects with weights between 120 and 220 pounds, the monitoring system can estimate that there are nine people standing in the living room. Based on the 300 pound increased weight of the sofa, the monitoring system can estimate that there are between one and three people sitting on the sofa.

The guests 220a in the living room may walk around the living room, enter and exit the living room and alternate between standing and sitting. Thus, the monitoring system might not be able to determine the exact number of guests 220a, but can estimate the number of guests 220a. In this example, the monitoring system estimates the number of people in the living room is between ten and fifteen.

The monitoring system can correlate the floor contact sensor 210a data with other sensor data. For example, if there are a large number of people gathered in a room, the temperature of the room will rise over time. Additionally, a door sensor can detect how many times the front door 230a opens and shuts, which can assist the monitoring system in approximating the number of guests.

The monitoring system analyzes the data 235a from the floor contact sensor 210a and the sensors at the property. The monitoring system makes a determination that there are approximately 10 to 15 people in the living room, and takes an action 240a. The monitoring system takes the action 240a of notifying the property owner of the high occupancy at the property. The monitoring system sends a notification to the property owner's mobile device that there are approximately 10 to 15 people gathered in the living room. This can prompt the property owner to visit the property or to call the occupants and ask if they are throwing a party, violating the terms of the lease.

In the example of FIG. 2B, a floor contact sensor 210b is installed in the living room of a rental property. To prevent damage to the property that can be caused by moving furniture and appliances, the property owners may write the terms of the rental agreement forbidding the movement of furniture and appliance at the property.

The floor contact sensor 210b can be used to monitor the location of furniture in the rental property. In the example of FIG. 2B, the occupants of the property move the sofa from location 215b to location 220b in the living room. The floor contact sensor 210b has a base state with the sofa at location 215b. The floor contact sensor 210b base state includes the sofa at a weight of 200 pounds spread over a floor area of 30 square feet at location 215b. When the occupants move the sofa to location 220b, the sensors at location 215b sense a rapid decrease of pressure to 0 pounds. The sensors at location 220b then sense a rapid increase of pressure to 200 pounds spread over an area of 30 square feet. The data collected by the floor contact sensor 210b can be used by the monitoring system to determine that a large piece of furniture was moved from location 215b to location 220b.

The monitoring system analyzes the data 235a from the floor contact sensor 210b. The monitoring system makes a determination that a piece of furniture has moved, and takes an action 240b. The monitoring system takes the action 240b of notifying the property owner of the furniture movement. The monitoring system sends a notification to the property owner's mobile device that furniture movement has been detected in the living room.

The floor contact sensor 210b can be used by property owners to detect other causes of damage as well. For example, the floor contact sensor can be configured to detect small pressure increases that may indicate a spill on the floor or carpet. The monitoring system can alert occupants to spills when they happen, so that the occupants can quickly clean the spill. This can help property owners identify the cause and timing of incidents that cause damage to the property. For example, an occupant may tell the property owner that a floor stain existed before move-in. The property owner can use the floor contact sensor data 235b to determine precisely when a spill occurred to cause the floor stain.

In the example of FIG. 2C, a floor contact sensor 210c is installed in the living room of a rental property. To reduce the power consumption of the property, the property owners or the occupants can configure the monitoring system to detect when a room is unoccupied, and to turn off unnecessary electrical or gas-powered equipment for that room. To improve security, the owners or occupants can also configure the monitoring system to detect when the property is unoccupied, and to automatically lock any unlocked external doors and arm the monitoring system when no one is home.

The floor contact sensor 210c can be used to track the movement of occupants to determine if the property, or a room within the property, is unoccupied. In the example of FIG. 2C, the occupant 215c departs the living room through the front door 230c. The floor contact sensor 210c tracks the footsteps of the occupant 215c, which lead through the living room to the front door 230c. The floor contact sensor 210c base state includes the sofa at a weight of 200 pounds spread over a floor area of 30 square feet. The floor contact sensor 210c detects the sofa at its normal weight.

Other sensors on the property collect data as well, and send that data to the control unit of the property monitoring system. For example, the HVAC system indicates that the thermostat 205c is set to 70 degrees, and the heat is on in the living room.

Appliance monitors, such as electrical current monitors connected to power cords, measure the current flowing to the living room lamp 225c and television 220c. The appliance monitors send data to the monitoring system indicating that the lamp 225c and television 220c are powered on. A door sensor connected to the front door 230c indicates that the front door 230c is shut but unlocked. The monitoring system status is unarmed.

The monitoring system analyzes the data 235c from the floor contact sensor 210c and other sensors at the property. Based on the occupant 215c's footsteps, the monitoring system determines that the occupant has departed the living room through the front door 230c. Based on the normal sofa weight measured by the floor contact sensor 210c, the monitoring system determines that no one is sitting on the sofa. Based on both of these determinations, the monitoring system concludes that the living room is unoccupied.

Based on the appliance monitor data, the monitoring system determines that the TV 220c and lamp 225c are powered on, and that the thermostat 205c is set to heat to 70 degrees. Based on the door sensor, the monitoring system determines that the front door is unlocked. The monitoring system makes a determination that the occupant 215c has departed the property without locking the front door 230c, while the TV 220c and lamp 225c are powered on, the thermostat 205c is set to heat the living room to 70 degrees, and the monitoring system is unarmed.

The monitoring system can take one or more actions 240c based on analyzing the data 235c. For example, the monitoring system can take the action 240c of sending a notification to the occupant's mobile device. The notification can request confirmation that the monitoring system should automatically turn off the TV 220c and lamp 225c, adjust the thermostat 205c, lock the front door 230c, and arm the monitoring system.

The example of FIG. 2C can be extended to include any automatic operation of appliances or equipment based on the occupancy of rooms within a property. For example, a monitoring system can be configured to automatically turn on lights and turn on heat or air conditioning in a room as a person approaches the room, based on footsteps detected by a floor monitor. Likewise, a monitoring system can be configured to automatically turn off lights and turn off heat or air conditioning when a person departs a room, based on the detected footsteps.

In a bathroom, floor contact sensing incorporated into a tile floor can integrate with automatic water control. For example, if the floor contact sensor detects an occupant standing near a shower, the monitoring system can automatically turn the shower on to a comfortable temperature, and turn on the bathroom ventilation system. Likewise, if a person steps up to a bathroom vanity, monitoring system can automatically start the flow of water from a faucet. When the floor contact sensor detects footsteps walking away from the vanity, the monitoring system can automatically stop the water from the faucet.

In another example, to conserve energy, heated floor tiles can turn on their heating element only when a person is standing on them. Each tile can include one or more heating element, and the system could be used to provide heating precisely where the resident is standing. In a piezo resistive solution, the change in resistance can be used directly to both sense the person's location and to increase the power dispersed at a given tile. The floor heat can shut off if no one is standing in the bathroom.

In a bedroom, floor contact sensing can detect when a person goes to bed at night. For example, based on detecting footsteps approaching a bed, and an increase in the weight of the bed, the monitoring system can be programmed to automatically shut off lights, turn on a speaker playing sleep sounds, and lower the thermostat heat setting.

Figure 3:
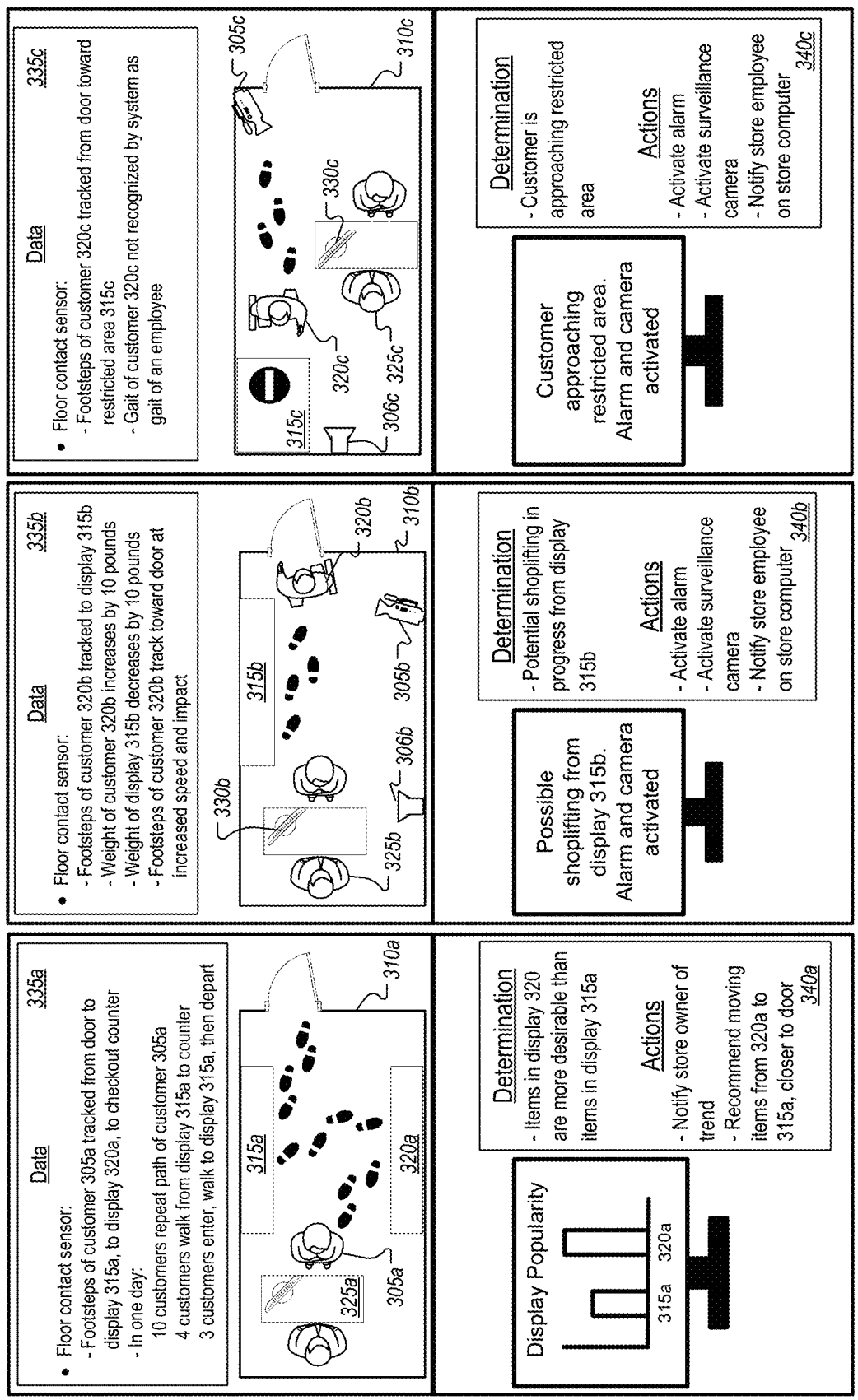
FIGS. 3A-3C are diagrams illustrating examples of commercial property control and configuration based on floor contact monitoring.

FIG. 3A-3C are diagrams illustrating examples of commercial property control and configuration based on floor contact monitoring.

In the example of FIG. 3A, a floor contact sensor 310a is installed in a retail property. The retail property can be, for example, a store that stocks and displays goods, and sells the goods from the store. To increase the sales from the store, the store owner can configure the monitoring system to detect customer foot-traffic patterns within the store, and to generate reports on the comparative popularity of displays in the store.

In the example of FIG. 3A, customer 305a enters the store, walks to display 315a, walks to display 320a, picks up an item to purchase, then walks to the checkout counter 325a to make the purchase. The floor contact sensor can track the footstep path of customer 305a based on her weight, walking gait, and footstep size measured when she enters the store. The floor contact sensor can also track the amount of time that customer spent looking at display 315a, and the amount of time spent looking at display 320a. Additionally, the floor contact sensor can detect the reduction of the weight of display 320a and the increase of the weight of customer 305a when customer 305a removes an item from display 320a.

The monitoring system analyzes the data 335a from the floor contact sensor 310a. Based on the customer 305a's footsteps and weight tracking, the monitoring system determines that the occupant selected to purchase an item from display 320a.

The floor contact sensor 310a detects footstep patterns for all customers who enter the store over a period of time such as a day, week, or month. The monitoring system can aggregate the data for all customers. In an example day, the monitoring system determines that ten customers repeat the same walking path as customer 305a. The same day, four customers walk to display 315a, pick up an object, and then walk to the checkout counter 325a. Three customers walk to display 315a and then leave the store.

Based on the aggregated floor contact sensor data 335a, the monitoring system concludes that display 320a contains items that are more desirable than display 315a. The monitoring system takes the action 340a of notifying the store owner of the observed trend. In this case, the monitoring system produces a report indicating that display 320a is more popular than display 315a.

The monitoring system can make a recommendation to the store owner to move items from display 320a to display 315a. Since display 315a is closer to the doorway, the items from display 315a are more frequently seen from outside of the store, and are the first items that customers see when they enter the store. By moving items from display 320a to display 315a, the store owner may be able to increase the amount of foot traffic in the store, increase the percentage of customers who make a purchase, and satisfy customers by making the most desirable items easy to find upon entering the store.

The store owner can also use the floor contact sensor data 335a for other purposes. For example, if the store owner wants to promote a certain product, the store owner can place the product in a high traffic area in the store. If there are certain areas of the store where crowds form, the store owner can spread out high-interest merchandise to other areas of the store to reduce the crowding.

The store owner can configure the monitoring system to take automatic actions based on customer foot traffic. For example, the monitoring system can be configured to automatically activate lighting, sounds, and/or fragrance as a customer approaches a display. This would allow the store owner to save energy by only turning on certain lighting, sounds, and fragrances when a customer is near a display.

While customer foot traffic can be obtained from other means such as door entry sensors and surveillance cameras, a floor contact sensor provides more detailed data and can offer more automation. Surveillance cameras may be blocked by objects and people, and therefore may not be able to capture images from an entire property. Additionally, while camera footage can be used to estimate the occupancy of a store, it would be difficult to use camera footage to track a customer's path through a store. Floor contact sensor data 335a can provide detailed information on each customer, such as when they enter, which displays they examine, how long they look at each display, and if they ultimately make a purchase before leaving.

In the example of FIG. 3B, a floor contact sensor 310b is installed in a retail property. To protect the store from shoplifting, the store owner can configure the monitoring system to detect customer foot traffic patterns within the store that may indicate shoplifting, and to generate alerts to notify store employees of shoplifting.

In the example of FIG. 3B, a shoplifter 320b enters the store, walks to a display 315b, takes an item off the shelf, then runs toward the exit. The floor contact sensor 310b can track the footstep path of shoplifter 320b based on his weight and footstep size measured when he enters the store. The floor contact sensor 310b can also detect the shoplifter 320b's gait, including the speed of his footsteps and the level of impact with the floor. The shoplifter 320b's gait changes when he switches from walking to running. The floor contact sensor 310b can detect the reduction of the weight of display 315b and the increase of the weight of shoplifter 320b when the shoplifter 320b removes an item from the display 315b.

The monitoring system analyzes the data 335b from the floor contact sensor 310b. Based on the shoplifter 320b's footstep path, increase in weight, and shift in gait from walking to running, the monitoring system determines that the shoplifter is attempting to remove an item from the store without paying.

Based on the determination that shoplifter 320b is attempting to shoplift, the monitoring system takes one or more actions 340b. The monitoring system can take the action 340b of notifying the store employee 325b of the possible shoplifting through a notification on the store computer 330b. The monitoring system can also automatically activate an alarm 306b, turn on a surveillance camera 305b, and/or notify authorities.

If the store employee 325b is not able to react and stop the shoplifter 320b, the floor contact sensor data 335b can be referenced afterwards to help identify a suspect. The floor contact sensor data 335b includes weight and footstep size information that can help authorities identify the shoplifter. Additionally, the exact time of the incident can be determined from the floor contact sensor data 335b indicating when the item was removed from display 315b, and when the shoplifter 320b started to run. The store employee can look at surveillance camera 305b video footage from that exact time to help identify the shoplifter 320b.

In the example of FIG. 3C, a floor contact sensor 310c is installed in a commercial property. The commercial property can be any commercial property that has an area 315c that is off-limits to customers. For example, the area 315c may be off-limits to customers because it is dangerous, or because it contains valuable or delicate items. To prevent customers from entering the restricted area, the property owner can configure the monitoring system to detect customer foot-traffic patterns within the property that indicate someone approaching the restricted area 315c.

In the example of FIG. 3C, a customer 320c enters the property and walks past the employee 325c toward a restricted area 315c. The floor contact sensor can track the footstep path of customer 320c based on his weight, walking gait, and footstep size measured when he enters the store.

The monitoring system can be programmed to recognize employee walking patterns in order to differentiate customers from employees. This can allow employees to walk into the restricted area 315c without triggering alerts.

The monitoring system analyzes the data 335c from the floor contact sensor 310c. Based on the customer 320c's path, the monitoring system determines that the customer 320c is approaching the restricted area 315c. This can allow a store employee 325c to react and prevent the customer 320c from entering the restricted area 315c, before he arrives at the restricted area 315c and opens the door.

Based on the determination that the customer 320*c* is approaching the restricted area 315*c*, the monitoring system takes one or more actions 340*c*. The monitoring system can take the action 340*c* of notifying the store employee 325*c* of the customer's path, through a notification on the store computer 330*c*. The monitoring system can also automatically activate an alarm 306*c* and/or turn on a surveillance camera 305*c*. Additionally, the monitoring system can activate a speaker that warns the customer 320*c* that he or she is approaching a restricted area.

In some implementations, it may be desirable to differentiate individuals on a property to the floor monitor. For example, on a commercial property, certain people, such as employees, may be allowed in certain areas, while customers are not allowed in those areas. In these implementations, special shoes or shoe covers can be worn by individuals to identify that individual to the floor monitor.

For example, in an assisted living or medical facility, it may be desirable to differentiate employees from patients. In this case, employees can wear a certain shoe covering, while patients can wear different shoe coverings. If a patient wanders into an off-limits area, the floor contact sensor can send the data to the monitoring system, which can generate a notification to the staff.

A shoe covering identification system can also be used to further differentiate individuals. For example, in an assisted living facility, kitchen staff may not be allowed in residential areas of the facility. Patients in a certain wing of the facility may not be allowed in other wings of the facility. Different categories of shoe coverings can be used to enable the floor contact sensor to detect when someone enters an area where they are not allowed.

In addition to, or instead of, shoe coverings, employees can wear trackers to identify themselves to the monitoring system as employees. For example, an employee can wear a certain wristband or shoe clip that identifies the employee to the monitoring system. The wristband can include various sensors such as GPS sensors. The wristband can also include transmitters such as ultrasonic sound transmitters or radio frequency transmitters that emit signals specific to that employee. If an employee approaches an area of a property that is off-limits to non-employees, the floor contact sensor sends the data to the monitoring system. The monitoring system can correlate the floor contact sensor data with data from the employee wristband. For example, the monitoring system may determine that the employee's GPS location corresponds to the floor contact sensor's detected location of movement. The monitoring system may also determine that ultrasonic receivers and/or radio frequency receivers installed near the off-limits area are detecting transmitted signals from the employee's wristband. The monitoring system can correlate the floor contact sensor data and employee tracker data to determine that the person approaching the off-limits area of the property is an employee, and can determine to take no action.

The floor contact sensor can be used to monitor employee activity in a business setting. For example, the owner of a large retail store may require that the employees circulate throughout the store to help customers. The floor contact sensor can be used to track employee activity and make sure that all areas of the store are evenly covered.

The floor contact sensor can also be used for occupational health purposes. For example, a floor contact sensor can monitor how long an employee has been sitting, how long they have been standing, and how long it has been since the employee worked without taking a break. The monitoring system can generate periodic reports for the employee and the employer to review. The monitoring system can also generate alerts to employees notifying them when it is time for a break, based on how long they have been standing, or how long they have been in one location.

The examples of FIGS. 3A-3C can also be applied to home-based applications. There may be certain areas of a residential areas that are designated as "off limits." In some cases, the areas may be off limits only to certain residents, only at certain times, or both. For example, a pet may not be allowed in a bedroom. Additionally, children may be kept away from hazards such as pools, stoves, and fireplaces. Children might not be allowed near a liquor cabinet at any time, and might be allowed near a refrigerator only during the day time.

A floor contact sensor can be used to monitor for specific people or pets approaching dangerous or off-limits areas. For example, if a pet enters an off-limits area, the monitoring system can activate an automated speaker that emits a high-pitched sound, so that the pet then leaves the area. Likewise, if a child approaches a fireplace, the monitoring system can activate an alarm to notify adults that the child is approaching a dangerous area.

In some examples, based on floor contact sensor data indicating a person in or approaching an off-limits area, the monitoring system can send a command to one or more cameras to capture images of the area. In some cases, the resident can input rules and settings that can vary depending on factors such as a time of day, a day of week, an occupancy of the property, etc. For example, the resident may input a setting that the monitoring system should capture images of any person approaching the refrigerator after ten o'clock at night on weekdays, and after eleven o'clock at night on weekends. In another example, the resident may input a setting that the monitoring system should capture images of any person standing in front of the refrigerator for longer than one minute.

In some examples, based on floor contact sensor data indicating a change in weight, the monitoring system can send a command to one or more cameras to capture images of the area. For example, a floor contact sensor can be installed or placed under a liquor cabinet. Floor contact sensor data may indicate a decrease in weight of the liquor cabinet. The resident may input a setting that in response to detecting the decrease in weight of the liquor cabinet, the monitoring system should send a command to one or more cameras to capture images of the liquor cabinet. The cameras may capture images for a set period of time, e.g., one minute, or until triggered to stop capturing images by detection of an event or by a command from the monitoring system.

FIGS. 4A-4D show example grid patterns than can be used for a floor contact monitor. The segment of the floor contact sensor in FIGS. 4A-4D includes a 6 by 6 square grid pattern. In this example, each square of the grid indicates one tile. Dark tiles indicate high levels of pressure, lighter tiles indicate lower levels of pressure, and white tiles indicate no detected pressure.

Figure 4:
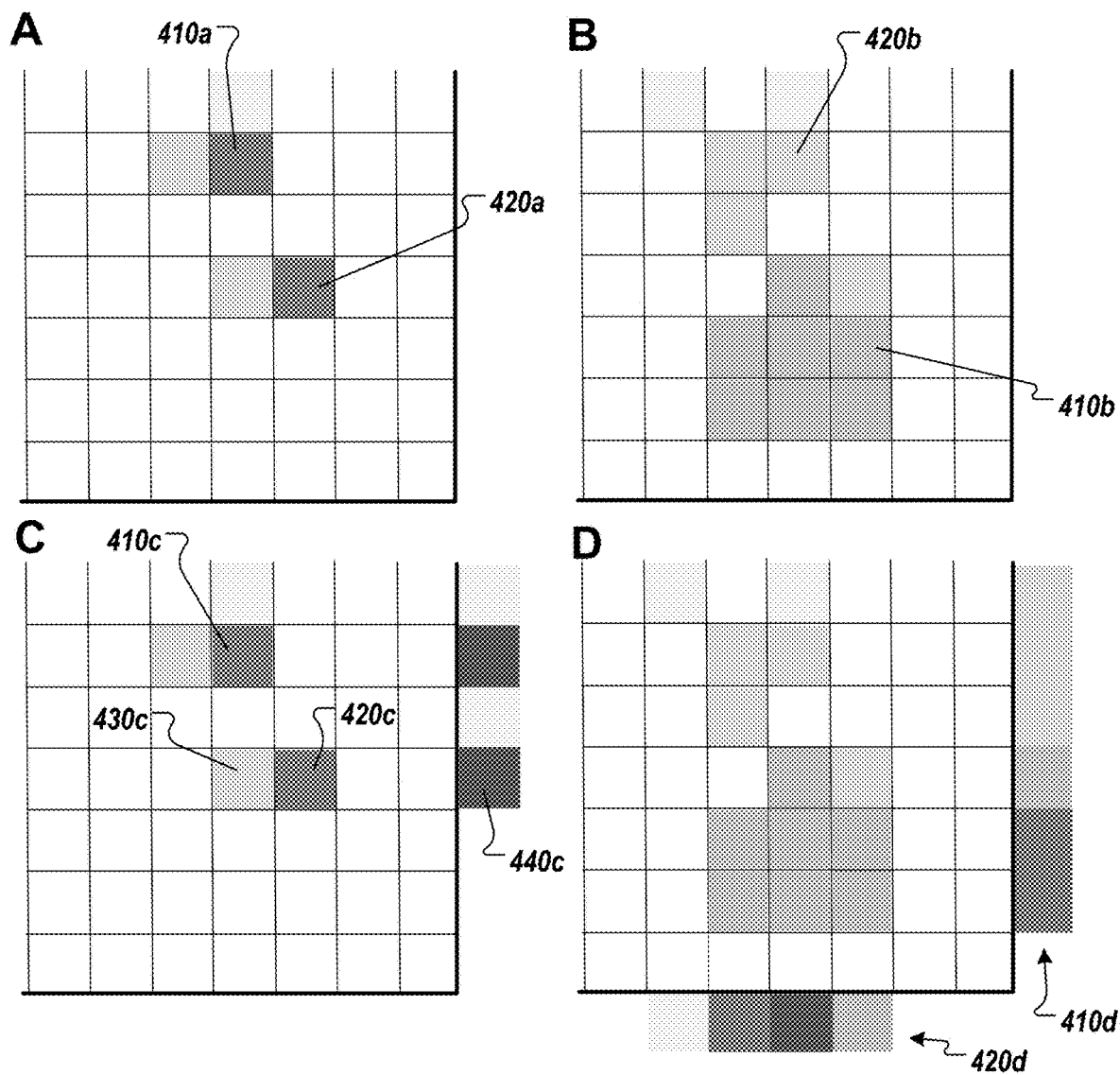
FIGS. 4A-4D are illustrations of example grid patterns that can be used for floor contact sensors.

The grid pattern shown in FIG. 4 can also be used for carpet pads or wood floor underlayment. When embedded in a carpet pad or underlayment, the individual sensors can be spaced in a grid-like pattern. In the example of a carpet pad or underlayment, each square would represent one sensor within the sensor array.

FIG. 4A shows an example of individual tile readouts for a person standing. The system would typically sense a standing person's weight as one or two areas distributed over the number of tiles that their feet covered. Two dark tiles 410*a* and 420*a* indicate the highest pressure locations of an individual's two feet while the individual is standing.

Should the individual slip and fall, the system could first measure the impact directly across whichever tiles they fell upon. The measured impact could be used to estimate the severity of a fall. The measured impact could also differentiate between a fall and someone lying on the ground, as for exercise.

After a fall, the individual's weight would be distributed over more tiles if the individual is laying prone. FIG. 4B shows an example of individual tile readouts for a person laying on the floor. The darker area 410*b* likely indicates the location of the heavier torso, while lighter area 420B might indicate the location of the lighter limbs.

If the pressure measurements remain constant for a period of time after the fall, the constant pressure readings could indicate that the individual is unconscious or otherwise immobile. The floor contact sensor can also observe pressure variations indicating movement while prone, or local increases in pressure as the individual attempts to rise from the ground using their hands, feet, and other points of contact. If the pressure readings indicate that the person has been lying on the floor for greater than a threshold period of time, such as several minutes, the monitoring system can request assistance from a caregiver or emergency personnel.

In FIGS. 4A and 4B, each individual tile transmits its measured pressure to the control unit of the monitoring system. In FIGS. 4C and 4D, the floor contact sensor transmits data to the control unit only through the edges of the floor monitor. To do this, the floor contact sensor adds the pressure in each row and column of sensors in the array.

In FIG. 4C, an individual is standing on the floor, with his or her feet exerting the most pressure on tiles 410*c* and 420*c*. The pressure measured in each column and row of the array are added together. For example, the pressure on tile 420*c* is added to the pressure on tile 430*c* to obtain the total pressure for that row, indicated by the dark square 440*c*. In the example in FIG. 4C, the floor contact sensor row and column totals result in two distinct points of contact in both rows and columns.

In FIG. 4D, an individual is laying on the floor, with his or her body exerting pressure across multiple tiles. The pressure measured in each column and row of the array are added together. The summation of rows 410*d* and columns 420*d* in FIG. 4D is less distinctive than the summations in 4C, because the weight of the body is more evenly distributed across the floor. The floor contact sensor sends the row and column summation data to the monitoring system, which can identify that a person is laying on the floor.

Figure 5:
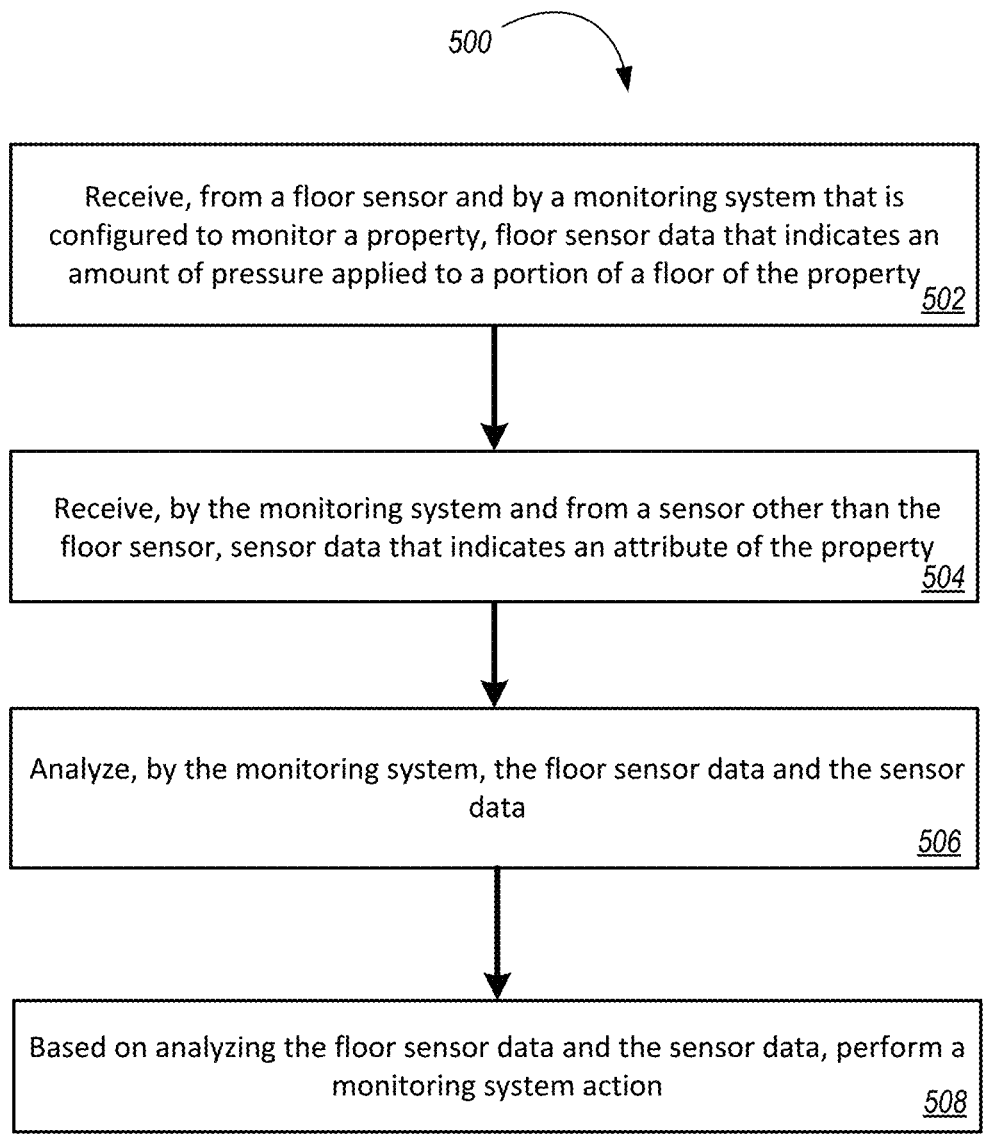
FIG. 5 is a flow chart illustrating an example of a process for property control and configuration based on floor contact monitoring.

FIG. 5 is a flow chart illustrating an example of a process for property control and configuration based on floor contact monitoring. Process 500 can be performed by one or more computer systems, for example, the monitoring server 150 of system 100. In some implementations, some or all of the process can be performed by the control unit 135 of the system 100, or by another computer system located at the monitored property.

Briefly, process 500 includes receiving floor sensor data, and sensor data from a sensor other than the floor sensor. Process 500 also includes analyzing the floor sensor data and the sensor data. Process 500 includes performing a monitoring system action in response to analyzing the floor sensor data and the sensor data.

In more detail, the process 500 includes receiving, from a floor sensor and by a monitoring system that is configured to monitor a property, floor sensor data that indicates an amount of pressure applied to a portion of a floor of the property (502). In some examples, the floor sensor is integrated into a floor surface. The floor surface can include, for example, a tile, a carpet, a mat, a floorboard, a pad, or an underlayment. In some examples, the floor of the property includes tiles. In these examples, the floor sensor can include pressure sensors, with each pressure sensor integrated into one of the tiles. Each pressure sensor can output a measured amount of pressure applied to the respective tile. In some examples, the floor sensor can include a number of strain gauges, fiber optic sensors, or capacitive sensors. In some examples, the amount of pressure applied to the portion of the floor of the property can include an indication of either a presence or absence of pressure applied to the portion of the floor.

A floor contact sensor can be attached to any type of flooring such as a carpet, tile, or floorboard. The floor contact sensor can collect data related to residents' activities based on sensing contact with the floor. For example, the floor contact sensor can detect the pressure of the resident's feet on the floor. The floor contact sensor uses pressure sensors to detect movement and weight distribution. Floor contact sensors provide, to the monitoring system, data related to the contact of people, pets, and objects with floors within the property. For example, floor contact sensors located in a room of the property can collect data that can be processed to determine the number of people in the room. Floor contact sensors can also detect and identify various activities such as walking, running, jumping, or falling.

The process 500 includes receiving, by the monitoring system and from a sensor other than the floor sensor, sensor data that indicates an attribute of the property (504). The sensor can be, for example, a camera, a motion sensor, a microphone, a thermometer, a humidity sensor, a GPS tracker, or a water flow sensor. Sensor data can include motion detector data from areas around the property, indicating the locations and movements of residents. Sensor data can also include temperature data from various rooms of the property, and water flow meter data regarding the flow of water to and from sinks, showers, and toilets on the property. Sensor data can include data from sensors such as humidity sensors, light detectors, and vehicle location trackers.

The process 500 includes analyzing, by the monitoring system, the floor sensor data and the sensor data (506). In some examples, the monitoring system can generate footstep data. The footstep data can include a number of footsteps taken on the portion of the floor during a period of time. For example, the footstep data may indicate that thirty steps in the bedroom were detected on Wednesday while the system was armed. The footstep data can also include a path of footsteps taken on the portion of the floor during the period of time. For example, the footstep data may indicate that a path of footsteps went in a straight line across the kitchen. The footstep data can also include a gait pattern of the person, a weight of the person, and/or a foot size of the person. For example, the footstep data may indicate that resident 115 currently weighs one hundred and eighty pounds. In a general example of the above, the monitoring server 150 can determine footstep data 145 for the resident 115. The footstep data 145 can include the number of steps taken by the resident 115 over the course of a day.

The process 500 includes, based on analyzing the floor sensor data and the sensor data, performing a monitoring system action (508). In some examples, the monitoring system action can include activating one or more cameras to capture an image of an area of the property that includes the portion of the floor. In some examples, the monitoring system can include identifying, using image analysis, a presence of a person in the image, and determining, based on analyzing the floor sensor data, a weight of the person in the image.

The monitoring system can also perform an action of dynamically controlling and configuring devices and components of a property based on floor contact sensor data. For example, the monitoring system can use the data provided by the floor contact sensor to adjust the lighting or temperature within certain areas of the property, to adjust the status of the monitoring system, or to turn on or off appliances and sensors based on the location and activities of residents.

In some examples, the monitoring system can determine, based on the footstep data, that the number of footsteps taken on the portion of the floor during the period of time deviates from an expected number of footsteps taken on the portion of the floor during the period of time. The monitoring system can perform the monitoring system action by communicating, to a user device of a user, a notification indicating that the number of footsteps taken on the portion of the floor during the period of time deviates from the expected number of footsteps taken on the portion of the floor during the period of time.

For example, the monitoring system can determine, based on the data 145, that the number of footsteps taken by the resident 115 over the course of a day is two hundred footsteps, and is less than an expected number of footsteps of five hundred footsteps. In response to determining that the number of footsteps taken by the resident 115 is less than the expected number of footsteps, the monitoring system can communicate, e.g., to the mobile device 175 of the caregiver 170, the notification 165 indicating that the resident 115 has been less active than expected.

In some examples, the floor is located in a garage having a garage door operated by a garage door control device. The monitoring system can determine an amount of pressure applied to the portion of the floor by a vehicle. The monitoring system can detect, based on analyzing the floor sensor data, an increase in the amount of pressure applied to the portion of the floor by the vehicle. Based on detecting the increase in the amount of pressure applied to the portion of the floor by the vehicle, the monitoring system can determine that a person has entered the vehicle. In response to determining that the person has entered the vehicle, the monitoring system can communicate an instruction to the garage door control device to open the garage door.

For example, the monitoring system can determine a weight of 3,000 pounds applied to a floor sensor of a garage floor by a vehicle. The monitoring system can detect, based on analyzing the floor sensor data, an increase in the weight applied to the garage floor from 3,000 pounds to 3,200 pounds. Based on detecting the increase in the weight applied to the garage floor, the monitoring system can determine that a person weighing 200 pounds has entered the vehicle. In response to determining that the person weighing 200 pounds has entered the vehicle, the monitoring system can communicate an instruction to the garage door control device to open the garage door.

In some examples, the monitoring system can determine, based on analyzing the sensor data and the floor sensor data, that a person has fallen on the floor, and in response to determining that the person has fallen on the floor, perform a monitoring system action. For example, the monitoring server 150 may determine from footstep data 145 that resident 115 has fallen on the floor. Determining that the resident 115 has fallen on the floor can include determining that an impact pressure applied to the portion of the floor exceeded a threshold impact pressure. For example, the floor contact sensor 110 may determine that an impact pressure of one hundred pounds per square inch applied to a portion of the floor including area 410b exceeded a threshold impact pressure of eighty pounds per square inch. Based on the impact pressure exceeding the threshold impact pressure, the monitoring system can determine that the resident 115 has fallen on the floor.

Determining that the person has fallen on the floor can also include determining that a distribution of the amount of pressure applied to the portion of the floor indicates that a person is prone on the floor, and determining that a length of time that the person is prone on the floor exceeds a threshold length of time. For example, the floor contact sensor 110 can determine that a distribution of the amount of pressure applied to the portion of the floor including area 410b is 0.2 pounds per square inch averaged over an area of four square feet, and indicates that the resident 115 is prone on the floor. The floor contact sensor 110 can determine that a length of time of five minutes that the resident 115 is prone on the floor exceeds a threshold length of time of three minutes. Based on determining that the length of time exceeds the threshold length of time, the monitoring system can determine that the resident 115 has fallen on the floor.

In response to determining that the resident 115 has fallen on the floor, the monitoring system can perform a monitoring system action. For example, the monitoring system can perform an action such as sending a notification to the caregiver 170 or to emergency personnel indicating that the resident 115 has fallen on the floor. In some examples, in response to determining that the resident 115 has fallen on the floor, the monitoring system can activate a personal assistant electronic device. The personal assistant can ask the resident 115 if the resident 115 needs assistance. If the resident 115 responds affirmatively, or fails to respond, the monitoring system can send a notification to the caregiver 170 or to emergency personnel.

In some examples, the monitoring system can determine, based on analyzing the sensor data and the floor sensor data, an occupancy of a portion of the property. The monitoring system can determine that the occupancy of the portion of the property exceeds a threshold occupancy of the property. For example, analyzing the data from the floor contact sensor 210a can include determining that the occupancy of the living room is eleven people. The threshold occupancy of the property may be ten people. Therefore, the monitoring system can determine that the occupancy of the living room exceeds the threshold occupancy of the property. In response to determining that the occupancy of the living room exceeds the threshold occupancy of the property, the monitoring system can perform a monitoring system action, for example, by sending a notification to an owner of the property indicating that the occupancy exceeds the threshold occupancy.

In some examples, the monitoring system can determine a base state of the portion of the floor. The base state can include an amount of pressure applied to the portion of the floor by inanimate objects in the absence of human activity. The monitoring system can detect, based on analyzing the sensor data and the floor sensor data, a change in the amount of pressure applied to the portion of the floor in the absence of human activity. Based on detecting the change in the amount of pressure applied to the portion of the floor in the absence of human activity, the monitoring system can determine that a location of one or more inanimate objects has changed.

For example, the monitoring system can determine a base state of the living room, including an average pressure of seven pounds per square foot applied by the sofa to location 215*b* of the living room floor. The base state can be determined in the absence of human activity, e.g., when no person is present in the living room. Once the base state data is stored, the monitoring system can detect changes to the base state. For example, the monitoring system can detect a decrease in average applied pressure at the location 215*b* to zero pounds per square foot, and an increase in average applied pressure at location 220*b* to seven pounds per square foot. Based on detecting the change in the amount of pressure applied to locations 215*b* and 220*b* of the living room floor, the monitoring system can determine that a location of the sofa has changed from 215*b* to 220*b*. In response to determining that the location of the sofa has changed, the monitoring system can perform a monitoring system action, for example, by sending a notification to an owner of the property indicating that the location of the sofa has changed.

In some examples, the monitoring system can determine, based on the path of footsteps taken on the portion of the floor during the period of time, that the person is approaching an area of the property that is off limits to the person. The monitoring system can determine that the person is approaching an area of the property that is off limits to the person by identifying, based on analyzing sensor data, an identifiable feature of the person. The monitoring system can retrieve, from a database, one or more identifiable features indicating access to the area of the property and determine that the identifiable feature of the person does not match any of the identifiable features indicating access to the area of the property. The identifiable feature of the person can include, for example, an age, weight, facial identity, apparel, foot size, gait pattern, or visible access credential.

For example, the monitoring system can determine that the customer 320*c* is approaching restricted area 315*c*. The monitoring system can identify an identifiable feature of the customer 320*c*. For example, based on analyzing the floor sensor data, the monitoring system can determine a gait pattern of the customer 320*c*. Based on analyzing images captured by the surveillance camera 305*c*, the monitoring system can determine a facial identity of the customer 320*c*. The monitoring system can determine that the gait pattern of the customer 320*c* does not match the gait pattern of any person with access to the restricted area 315*c*, that the facial identity of the customer 320*c* does not match the facial identity of any person with access to the restricted area 315*c*, or both. Therefore, the monitoring system can determine that the customer 320*c* is approaching an area of the property that is off limits to the customer 320*c*. In response to determining that the customer 320*c* is approaching an area of the property that is off limits to the customer 320*c*, the monitoring system can perform a monitoring system action. For example, the monitoring system can perform the monitoring system action by activating the alarm 306*c*, activating the surveillance camera 305*c* to capture images of the restricted area 315*c*, or sending a notification to the employee 325*c* indicating that the customers 320*c* is approaching the restricted area 315*c*.

In some examples, the monitoring system can determine an amount of pressure applied to the portion of the floor by a furnishing storing a number of items. The monitoring system can detect, based on analyzing the floor sensor data, a reduction in the amount of pressure applied to the portion of the floor by the furnishing. Based on detecting the reduction in the amount of pressure applied to the portion of the floor by the furnishing, the monitoring system can determine that one or more of the items has been removed from the furnishing.

For example, the monitoring system can determine that a weight of the display 315*b* storing items is two hundred pounds. The monitoring system can detect, based on analyzing the floor sensor data of floor contact sensor 310*b*, a reduction in the weight of the display 315*b* from two hundred pounds to one hundred and eighty pounds. Based on detecting the reduction in the weight of the display 315*b*, the monitoring system can determine that an item weighing approximately twenty pounds was removed from the display 315*b*. In response to determining that the item weighting approximately twenty pounds was removed from the display 315*b*, the monitoring system can perform a monitoring system action, for example, by activating the alarm 306*b*, by activating the surveillance camera 305*b* to capture images of the display 315*b*, or by sending a notification to the employee 325*b* indicating that the item was removed from the display 315*b*.

In some examples, as a person walks through a room of a property, the monitoring server can receive floor contact sensor data indicating the weight, footstep size, footstep path, and gait of the person. The monitoring server can also receive motion sensor data indicating the person's movement, surveillance camera imagery of the person walking through the room, and audio data indicating the sound of the person walking. The monitoring server can correlate data from the sensors with floor contact sensor data to assess the activities of people on the property, and to detect any anomalies.

For example, the monitoring server can receive floor contact sensor data indicating the weight, footstep size, footstep path, and gait of the shoplifter 320*b*. The monitoring server can also receive camera images of the shoplifter 320*b* from the surveillance camera 305*b*. The monitoring server can correlate data from the surveillance camera 305*b* with the floor contact sensor data to assess the activities of the shoplifter 320*b*. For example, the monitoring server can determine that the shoplifter 320*b* removed an item from the display 315*b* and departed from the retail property. In response to determining that the shoplifter 320*b* removed the item from the display 315*b* and departed from the retail property, the monitoring system can perform a monitoring system action. For example, the monitoring system can perform the monitoring system action by sending the floor contact sensor data and the surveillance camera images to the employee 325*b*, or to emergency personnel, for use in identifying the shoplifter 320*b*.

Figure 6:
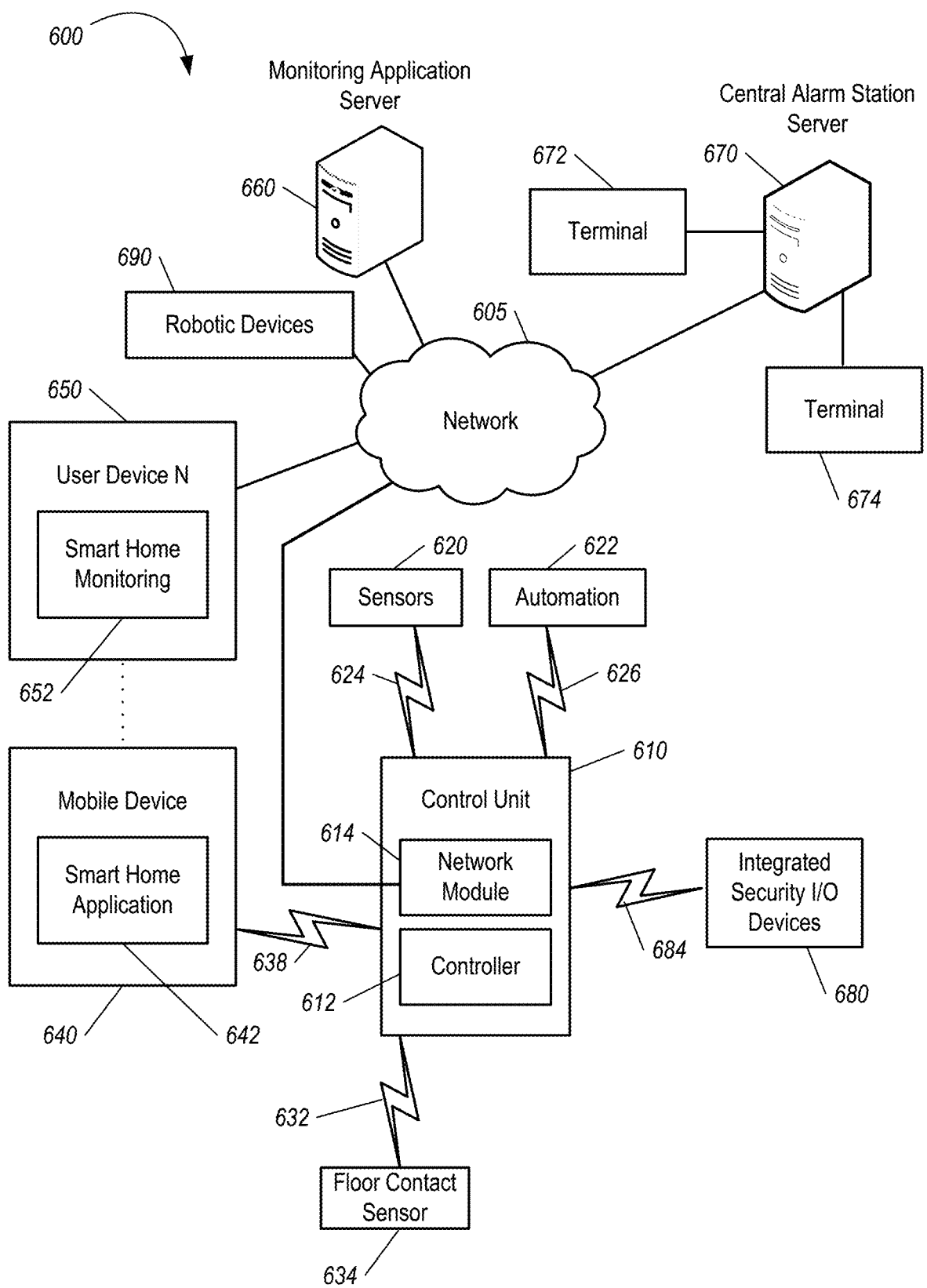
FIG. 6 is a diagram illustrating an example of a property monitoring system.

FIG. 6 is a diagram illustrating an example of a property monitoring system 600. The system 600 includes a network 605, a control unit 610, one or more user devices 640 and 650, a monitoring server 660, and a central alarm station server 670. In some examples, the network 605 facilitates communications between the control unit 610, the one or more user devices 640 and 650, the monitoring server 660, and the central alarm station server 670.

A floor contact sensor 634 connects to the network 605 through the control unit 610. The network 605 is configured to enable exchange of electronic communications between devices connected to the network 605. For example, the network 605 may be configured to enable exchange of electronic communications between the control unit 610, the one or more user devices 640 and 650, the monitoring server 660, and the central alarm station server 670. The network 605 may include, for example, one or more of the Internet, Wide Area Networks (WANs), Local Area Networks (LANs), analog or digital wired and wireless telephone networks (e.g., a public switched telephone network (PSTN), Integrated Services Digital Network (ISDN), a cellular network, and Digital Subscriber Line (DSL)), radio, television, cable, satellite, or any other delivery or tunneling mechanism for carrying data. The network 605 may include multiple networks or subnetworks, each of which may include, for example, a wired or wireless data pathway. The network 605 may include a circuit-switched network, a packet-switched data network, or any other network able to carry electronic communications (e.g., data or voice communications). For example, the network 605 may include networks based on the Internet protocol (IP), asynchronous transfer mode (ATM), the PSTN, packet-switched networks based on IP, X.25, or Frame Relay, or other comparable technologies and may support voice using, for example, VoIP, or other comparable protocols used for voice communications. The network 605 may include one or more networks that include wireless data channels and wireless voice channels. The network 605 may be a wireless network, a broadband network, or a combination of networks including a wireless network and a broadband network.

The control unit 610 includes a controller 612 and a network module 614. The controller 612 is configured to control a control unit monitoring system (e.g., a control unit system) that includes the control unit 610. In some examples, the controller 612 may include a processor or other control circuitry configured to execute instructions of a program that controls operation of a control unit system. In these examples, the controller 612 may be configured to receive input from sensors, floor monitors, or other devices included in the control unit system and control operations of devices included in the household (e.g., speakers, lights, doors, etc.). For example, the controller 612 may be configured to control operation of the network module 614 included in the control unit 610.

The network module 614 is a communication device configured to exchange communications over the network 605. The network module 614 may be a wireless communication module configured to exchange wireless communications over the network 605. For example, the network module 614 may be a wireless communication device configured to exchange communications over a wireless data channel and a wireless voice channel. In this example, the network module 614 may transmit alarm data over a wireless data channel and establish a two-way voice communication session over a wireless voice channel. The wireless communication device may include one or more of a LTE module, a GSM module, a radio modem, cellular transmission module, or any type of module configured to exchange communications in one of the following formats: LTE, GSM or GPRS, CDMA, EDGE or EGPRS, EV-DO or EVDO, UMTS, or IP.

The network module 614 also may be a wired communication module configured to exchange communications over the network 605 using a wired connection. For instance, the network module 614 may be a modem, a network interface card, or another type of network interface device. The network module 614 may be an Ethernet network card configured to enable the control unit 610 to communicate over a local area network and/or the Internet. The network module 614 also may be a voice band modem configured to enable the alarm panel to communicate over the telephone lines of Plain Old Telephone Systems (POTS).

The control unit system that includes the control unit 610 includes one or more sensors 620. For example, the monitoring system may include multiple sensors 620. The sensors 620 may include a lock sensor, a contact sensor, a motion sensor, or any other type of sensor included in a control unit system. The sensors 620 also may include an environmental sensor, such as a thermometer, a water sensor, a rain sensor, a wind sensor, a light sensor, a smoke detector, a carbon monoxide detector, an air quality sensor, etc.

The system 600 also includes one or more property automation controls 622 that communicate with the control unit 610 to perform monitoring. The property automation controls 622 are connected to one or more devices connected to the system 600 and enable automation of actions at the property. For instance, the property automation controls 622 may be connected to one or more lighting systems and may be configured to control operation of the one or more lighting systems. Also, the property automation controls 622 may be connected to one or more electronic locks at the property and may be configured to control operation of the one or more electronic locks (e.g., control Z-Wave locks using wireless communications in the Z-Wave protocol). Further, the property automation controls 622 may be connected to one or more appliances at the property and may be configured to control operation of the one or more appliances. The property automation controls 622 may include multiple modules that are each specific to the type of device being controlled in an automated manner. The property automation controls 622 may control the one or more devices based on commands received from the control unit 610. For instance, the property automation controls 622 may interrupt power delivery to a particular outlet of the property or induce movement of a smart window shade of the property.

In some examples, the system 600 includes one or more robotic devices 690. The robotic devices 690 may be any type of robot that are capable of moving and taking actions that assist in home monitoring. For example, the robotic devices 690 may include drones that are capable of moving throughout a property based on automated control technology and/or user input control provided by a user. In this example, the drones may be able to fly, roll, walk, or otherwise move about the property. The drones may include helicopter type devices (e.g., quad copters), rolling helicopter type devices (e.g., roller copter devices that can fly and/or roll along the ground, walls, or ceiling) and land vehicle type devices (e.g., automated cars that drive around a property). In some cases, the robotic devices 690 may be robotic devices 690 that are intended for other purposes and merely associated with the system 600 for use in appropriate circumstances. For instance, a robotic aerial drone may be associated with the monitoring system 600 as one of the robotic devices 690 and may be controlled to take action responsive to monitoring system events.

In some examples, the robotic devices 690 automatically navigate within a property. In these examples, the robotic devices 690 include sensors and control processors that guide movement of the robotic devices 690 within the property. For instance, the robotic devices 690 may navigate within the property using one or more cameras, one or more proximity sensors, one or more gyroscopes, one or more accelerometers, one or more magnetometers, a global positioning system (GPS) unit, an altimeter, one or more sonar or laser sensors, and/or any other types of sensors that aid in navigation about a space. The robotic devices 690 may include control processors that process output from the various sensors and control the robotic devices 690 to move along a path that reaches the desired destination and avoids obstacles. In this regard, the control processors detect walls or other obstacles in the property and guide movement of the robotic devices 690 in a manner that avoids the walls and other obstacles.

In addition, the robotic devices 690 may store data that describes attributes of the property. For instance, the robotic devices 690 may store a floorplan of a building on the property and/or a three-dimensional model of the property that enables the robotic devices 690 to navigate the property. During initial configuration, the robotic devices 690 may receive the data describing attributes of the property, determine a frame of reference to the data (e.g., a property or reference location in the property), and navigate the property based on the frame of reference and the data describing attributes of the property. Further, initial configuration of the robotic devices 690 also may include learning of one or more navigation patterns in which a user provides input to control the robotic devices 690 to perform a specific navigation action (e.g., fly to an upstairs bedroom and spin around while capturing video and then return to a home charging base). In this regard, the robotic devices 690 may learn and store the navigation patterns such that the robotic devices 690 may automatically repeat the specific navigation actions upon a later request.

In some examples, the robotic devices 690 may include data capture and recording devices. In these examples, the robotic devices 690 may include one or more cameras, one or more motion sensors, one or more microphones, one or more biometric data collection tools, one or more temperature sensors, one or more humidity sensors, one or more air flow sensors, and/or any other types of sensors that may be useful in capturing monitoring data related to the property and users at the property.

In some implementations, the robotic devices 690 may include output devices. In these implementations, the robotic devices 690 may include one or more displays, one or more speakers, and/or any type of output devices that allow the robotic devices 690 to communicate information to a nearby user.

The robotic devices 690 also may include a communication module that enables the robotic devices 690 to communicate with the control unit 610, each other, and/or other devices. The communication module may be a wireless communication module that allows the robotic devices 690 to communicate wirelessly. For instance, the communication module may be a Wi-Fi module that enables the robotic devices 690 to communicate over a local wireless network at the property. The communication module further may be a 900 MHz wireless communication module that enables the robotic devices 690 to communicate directly with the control unit 610. Other types of short-range wireless communication protocols, such as Bluetooth, Bluetooth LE, Z-wave, Zigbee, etc., may be used to allow the robotic devices 690 to communicate with other devices in the property. In some implementations, the robotic devices 690 may communicate with each other or with other devices of the system 600 through the network 605.

The robotic devices 690 further may include processor and storage capabilities. The robotic devices 690 may include any suitable processing devices that enable the robotic devices 690 to operate applications and perform the actions described throughout this disclosure. In addition, the robotic devices 690 may include solid state electronic storage that enables the robotic devices 690 to store applications, configuration data, collected sensor data, and/or any other type of information available to the robotic devices 690.

The robotic devices 690 can be associated with one or more charging stations. The charging stations may be located at predefined home base or reference locations at the property. The robotic devices 690 may be configured to navigate to the charging stations after completion of tasks needed to be performed for the monitoring system 600. For instance, after completion of a monitoring operation or upon instruction by the control unit 610, the robotic devices 690 may be configured to automatically fly to and land on one of the charging stations. In this regard, the robotic devices 690 may automatically maintain a fully charged battery in a state in which the robotic devices 690 are ready for use by the monitoring system 600.

The charging stations may be contact-based charging stations and/or wireless charging stations. For contact-based charging stations, the robotic devices 690 may have readily accessible points of contact that the robotic devices 690 are capable of positioning and mating with a corresponding contact on the charging station. For instance, a helicopter type robotic device 690 may have an electronic contact on a portion of its landing gear that rests on and mates with an electronic pad of a charging station when the helicopter type robotic device 690 lands on the charging station. The electronic contact on the robotic device 690 may include a cover that opens to expose the electronic contact when the robotic device 690 is charging and closes to cover and insulate the electronic contact when the robotic device is in operation.

For wireless charging stations, the robotic devices 690 may charge through a wireless exchange of power. In these cases, the robotic devices 690 need only locate themselves closely enough to the wireless charging stations for the wireless exchange of power to occur. In this regard, the positioning needed to land at a predefined home base or reference location in the property may be less precise than with a contact based charging station. Based on the robotic devices 690 landing at a wireless charging station, the wireless charging station outputs a wireless signal that the robotic devices 690 receive and convert to a power signal that charges a battery maintained on the robotic devices 690.

In some implementations, each of the robotic devices 690 has a corresponding and assigned charging station such that the number of robotic devices 690 equals the number of charging stations. In these implementations, the robotic devices 690 always navigate to the specific charging station assigned to that robotic device. For instance, a first robotic device 690 may always use a first charging station and a second robotic device 690 may always use a second charging station.

In some examples, the robotic devices 690 may share charging stations. For instance, the robotic devices 690 may use one or more community charging stations that are capable of charging multiple robotic devices 690. The community charging station may be configured to charge multiple robotic devices 690 in parallel. The community charging station may be configured to charge multiple robotic devices 690 in serial such that the multiple robotic devices 690 take turns charging and, when fully charged, return to a predefined home base or reference location in the property that is not associated with a charger. The number of community charging stations may be less than the number of robotic devices 690.

Also, the charging stations may not be assigned to specific robotic devices 690 and may be capable of charging any of the robotic devices 690. In this regard, the robotic devices 690 may use any suitable, unoccupied charging station when not in use. For instance, when one of the robotic devices 690 has completed an operation or is in need of battery charge, the control unit 610 references a stored table of the occupancy status of each charging station and instructs the robotic device 690 to navigate to the nearest charging station that is unoccupied.

The system 600 further includes one or more integrated security devices 680. The one or more integrated security devices may include any type of device used to provide alerts based on received sensor data. For instance, the one or more control units 610 may provide one or more alerts to the one or more integrated security input/output devices 680. Additionally, the one or more control units 610 may receive one or more sensor data from the sensors 620 and determine whether to provide an alert to the one or more integrated security input/output devices 680.

The sensors 620, the property automation controls 622, and the integrated security devices 680 may communicate with the controller 612 over communication links 624, 626, 632, and 684. The communication links 624, 626, 632, and 684 may be a wired or wireless data pathway configured to transmit signals from the sensors 620, the property automation controls 622, the floor contact sensor 634, and the integrated security devices 680 to the controller 612. The sensors 620, the property automation controls 622, the floor contact sensor 634, and the integrated security devices 680 may continuously transmit sensed values to the controller 612, periodically transmit sensed values to the controller 612, or transmit sensed values to the controller 612 in response to a change in a sensed value.

The communication links 624, 626, 632, and 684 may include a local network. The sensors 620, the property automation controls 622, the floor contact sensor 634, and the integrated security devices 680, and the controller 612 may exchange data and commands over the local network. The local network may include 802.11 "Wi-Fi" wireless Ethernet (e.g., using low-power Wi-Fi chipsets), Z-Wave, Zigbee, Bluetooth, "Homeplug" or other "Powerline" networks that operate over AC wiring, and a Category 5 (CAT5) or Category 6 (CAT6) wired Ethernet network. The local network may be a mesh network constructed based on the devices connected to the mesh network.

The monitoring server 660 is one or more electronic devices configured to provide monitoring services by exchanging electronic communications with the control unit 610, the one or more user devices 640 and 650, and the central alarm station server 670 over the network 605. For example, the monitoring server 660 may be configured to monitor events (e.g., alarm events) generated by the control unit 610. In this example, the monitoring server 660 may exchange electronic communications with the network module 614 included in the control unit 610 to receive information regarding events (e.g., alerts) detected by the control unit 610. The monitoring server 660 also may receive information regarding events (e.g., alerts) from the one or more user devices 640 and 650.

In some examples, the monitoring server 660 may route alert data received from the network module 614 or the one or more user devices 640 and 650 to the central alarm station server 670. For example, the monitoring server 660 may transmit the alert data to the central alarm station server 670 over the network 605.

The monitoring server 660 may store sensor data and other monitoring system data received from the monitoring system and perform analysis of the sensor data and other monitoring system data received from the monitoring system. Based on the analysis, the monitoring server 660 may communicate with and control aspects of the control unit 610 or the one or more user devices 640 and 650.

The monitoring server 660 may provide various monitoring services to the system 600. For example, the monitoring server 660 may analyze the sensor and other data to determine an activity pattern of a resident of the property monitored by the system 600. In some implementations, the monitoring server 660 may analyze the data for alarm conditions or may determine and perform actions at the property by issuing commands to one or more of the automation controls 622, possibly through the control unit 610.

The central alarm station server 670 is an electronic device configured to provide alarm monitoring service by exchanging communications with the control unit 610, the one or more mobile devices 640 and 650, and the monitoring server 660 over the network 605. For example, the central alarm station server 670 may be configured to monitor alerting events generated by the control unit 610. In this example, the central alarm station server 670 may exchange communications with the network module 614 included in the control unit 610 to receive information regarding alerting events detected by the control unit 610. The central alarm station server 670 also may receive information regarding alerting events from the one or more mobile devices 640 and 650 and/or the monitoring server 660.

The central alarm station server 670 is connected to multiple terminals 672 and 674. The terminals 672 and 674 may be used by operators to process alerting events. For example, the central alarm station server 670 may route alerting data to the terminals 672 and 674 to enable an operator to process the alerting data. The terminals 672 and 674 may include general-purpose computers (e.g., desktop personal computers, workstations, or laptop computers) that are configured to receive alerting data from a server in the central alarm station server 670 and render a display of information based on the alerting data. For instance, the controller 612 may control the network module 614 to transmit, to the central alarm station server 670, alerting data indicating that a sensor 620 detected motion from a motion sensor via the sensors 620. The central alarm station server 670 may receive the alerting data and route the alerting data to the terminal 672 for processing by an operator associated with the terminal 672. The terminal 672 may render a display to the operator that includes information associated with the alerting event (e.g., the lock sensor data, the motion sensor data, the contact sensor data, etc.) and the operator may handle the alerting event based on the displayed information.

In some implementations, the terminals 672 and 674 may be mobile devices or devices designed for a specific function. Although FIG. 6 illustrates two terminals for brevity, actual implementations may include more (and, perhaps, many more) terminals.

The one or more authorized user devices 640 and 650 are devices that host and display user interfaces. For instance, the user device 640 is a mobile device that hosts or runs one or more native applications (e.g., the smart home application 642). The user device 640 may be a cellular phone or a non-cellular locally networked device with a display. The user device 640 may include a cell phone, a smart phone, a tablet PC, a personal digital assistant ("PDA"), or any other portable device configured to communicate over a network and display information. For example, implementations may also include Blackberry-type devices (e.g., as provided by Research in Motion), electronic organizers, iPhone-type devices (e.g., as provided by Apple), iPod devices (e.g., as provided by Apple) or other portable music players, other communication devices, and handheld or portable electronic devices for gaming, communications, and/or data organization. The user device 640 may perform functions unrelated to the monitoring system, such as placing personal telephone calls, playing music, playing video, displaying pictures, browsing the Internet, maintaining an electronic calendar, etc.

The user device 640 includes a smart home application 642. The smart home application 642 refers to a software/firmware program running on the corresponding mobile device that enables the user interface and features described throughout. The user device 640 may load or install the smart home application 642 based on data received over a network or data received from local media. The smart home application 642 runs on mobile devices platforms, such as iPhone, iPod touch, Blackberry, Google Android, Windows Mobile, etc. The smart home application 642 enables the user device 640 to receive and process power and sensor data from the monitoring system.

The user device 650 may be a general-purpose computer (e.g., a desktop personal computer, a workstation, or a laptop computer) that is configured to communicate with the monitoring server 660 and/or the control unit 610 over the network 605. The user device 650 may be configured to display a smart home user interface 652 that is generated by the user device 650 or generated by the monitoring server 660. For example, the user device 650 may be configured to display a user interface (e.g., a web page) provided by the monitoring server 660 that enables a user to perceive data captured by the floor contact sensor 634 and/or reports related to the monitoring system. Although FIG. 6 illustrates two user devices for brevity, actual implementations may include more (and, perhaps, many more) or fewer user devices.

The smart home application 642 and the smart home user interface 652 can allow a user to interface with the property monitoring system 600, for example, allowing the user to view monitoring system settings, adjust monitoring system parameters, customize monitoring system rules, and receive and view monitoring system messages.

In some implementations, the one or more user devices 640 and 650 communicate with and receive monitoring system data from the control unit 610 using the communication link 638. For instance, the one or more user devices 640 and 650 may communicate with the control unit 610 using various local wireless protocols such as Wi-Fi, Bluetooth, Z-wave, Zigbee, HomePlug (ethernet over power line), or wired protocols such as Ethernet and USB, to connect the one or more user devices 640 and 650 to local security and automation equipment. The one or more user devices 640 and 650 may connect locally to the monitoring system and its sensors and other devices. The local connection may improve the speed of status and control communications because communicating through the network 605 with a remote server (e.g., the monitoring server 660) may be significantly slower.

Although the one or more user devices 640 and 650 are shown as communicating with the control unit 610, the one or more user devices 640 and 650 may communicate directly with the sensors 620 and other devices controlled by the control unit 610. In some implementations, the one or more user devices 640 and 650 replace the control unit 610 and perform the functions of the control unit 610 for local monitoring and long range/offsite communication.

In other implementations, the one or more user devices 640 and 650 receive monitoring system data captured by the control unit 610 through the network 605. The one or more user devices 640, 650 may receive the data from the control unit 610 through the network 605 or the monitoring server 660 may relay data received from the control unit 610 to the one or more user devices 640 and 650 through the network 605. In this regard, the monitoring server 660 may facilitate communication between the one or more user devices 640 and 650 and the monitoring system 600.

In some implementations, the one or more user devices 640 and 650 may be configured to switch whether the one or more user devices 640 and 650 communicate with the control unit 610 directly (e.g., through link 638) or through the monitoring server 660 (e.g., through network 605) based on a location of the one or more user devices 640 and 650. For instance, when the one or more user devices 640 and 650 are located close to the control unit 610 and in range to communicate directly with the control unit 610, the one or more user devices 640 and 650 use direct communication. When the one or more user devices 640 and 650 are located far from the control unit 610 and not in range to communicate directly with the control unit 610, the one or more user devices 640 and 650 use communication through the monitoring server 660.

Although the one or more user devices 640 and 650 are shown as being connected to the network 605, in some implementations, the one or more user devices 640 and 650 are not connected to the network 605. In these implementations, the one or more user devices 640 and 650 communicate directly with one or more of the monitoring system components and no network (e.g., Internet) connection or reliance on remote servers is needed.

In some implementations, the one or more user devices 640 and 650 are used in conjunction with only local sensors and/or local devices in a property. In these implementations, the system 600 includes the one or more user devices 640 and 650, the sensors 620, the property automation controls 622, the floor contact sensor 634, and the robotic devices 690. The one or more user devices 640 and 650 receive data directly from the sensors 620, the property automation controls 622, the floor contact sensor 634, and the robotic devices 690 (i.e., the monitoring system components) and sends data directly to the monitoring system components. The one or more user devices 640, 650 provide the appropriate interfaces/processing to provide visual surveillance and reporting.

In other implementations, the system 600 further includes network 605 and the sensors 620, the property automation controls 622, the floor contact sensor 634, and the robotic devices 690 are configured to communicate sensor and power data to the one or more user devices 640 and 650 over network 605 (e.g., the Internet, cellular network, etc.). In yet another implementation, the sensors 620, the property automation controls 622, the floor contact sensor 634, and the robotic devices 690 (or a component, such as a bridge/router) are intelligent enough to change the communication pathway from a direct local pathway when the one or more user devices 640 and 650 are in close physical proximity to the sensors 620, the property automation controls 622, the floor contact sensor 634, and the robotic devices 690 to a pathway over network 605 when the one or more user devices 640 and 650 are farther from the sensors 620, the property automation controls 622, the floor contact sensor 634, and the robotic devices 690. In some examples, the system leverages GPS information from the one or more user devices 640 and 650 to determine whether the one or more user devices 640 and 650 are close enough to the monitoring system components to use the direct local pathway or whether the one or more user devices 640 and 650 are far enough from the monitoring system components that the pathway over network 605 is required. In other examples, the system leverages status communications (e.g., pinging) between the one or more user devices 640 and 650 and the sensors 620, the property automation controls 622, the floor contact sensor 634, and the robotic devices 690 to determine whether communication using the direct local pathway is possible. If communication using the direct local pathway is possible, the one or more user devices 640 and 650 communicate with the sensors 620, the property automation controls 622, the floor contact sensor 634, and the robotic devices 690 using the direct local pathway. If communication using the direct local pathway is not possible, the one or more user devices 640 and 650 communicate with the monitoring system components using the pathway over network 605.

In some implementations, the system 600 provides end users with access to the floor contact data captured by the floor contact sensor 634 to aid in decision making. The system 600 may transmit the floor contact data captured by the floor contact sensor 634 over a wireless WAN network to the user devices 640 and 650. Because transmission over a wireless WAN network may be relatively expensive, the system 600 can use several techniques to reduce costs while providing access to significant levels of useful visual information (e.g., compressing data, down-sampling data, sending data only over inexpensive LAN connections, or other techniques).

The described systems, processes, and techniques may be implemented in digital electronic circuitry, computer hardware, firmware, software, or in combinations of these elements. Apparatus implementing these techniques may include appropriate input and output devices, a computer processor, and a computer program product tangibly embodied in a machine-readable storage device for execution by a programmable processor. A process implementing these techniques may be performed by a programmable processor executing a program of instructions to perform desired functions by operating on input data and generating appropriate output. The techniques may be implemented in one or more computer programs that are executable on a programmable system including at least one programmable processor coupled to receive data and instructions from, and to transmit data and instructions to, a data storage system, at least one input device, and at least one output device. Each computer program may be implemented in a high-level procedural or object-oriented programming language, or in assembly or machine language if desired; and in any case, the language may be a compiled or interpreted language. Suitable processors include, by way of example, both general and special purpose microprocessors. Generally, a processor will receive instructions and data from a read-only memory and/or a random-access memory. Storage devices suitable for tangibly embodying computer program instructions and data include all forms of non-volatile memory, including by way of example semiconductor memory devices, such as Erasable Programmable Read-Only Memory (EPROM), Electrically Erasable Programmable Read-Only Memory (EEPROM), and flash memory devices; magnetic disks such as internal hard disks and removable disks; magneto-optical disks; and Compact Disc Read-Only Memory (CD-ROM). Any of the foregoing may be supplemented by, or incorporated in, specially designed ASICs (application-specific integrated circuits).

It will be understood that various modifications may be made. For example, other useful implementations could be achieved if steps of the disclosed techniques were performed in a different order and/or if components in the disclosed systems were combined in a different manner and/or replaced or supplemented by other components. Accordingly, other implementations are within the scope of the disclosure.

What is claimed is:

1. A monitoring system that is configured to monitor a property, the monitoring system comprising:
    a sensor that is configured to generate sensor data that indicates an attribute of the property, wherein the sensor comprises one of a thermometer, a camera, a microphone, an appliance monitor, or a water flow meter, and the sensor data comprises one of temperature data, camera data, microphone data, appliance monitor data, or water flow meter data;
    a floor sensor that is configured to generate floor sensor data that indicates an amount of pressure applied to a portion of a floor of the property; and
    a monitor control unit that is configured to:
        receive, from the sensor, the sensor data;
        receive, from the floor sensor, the floor sensor data;
        analyze the sensor data and the floor sensor data;
        determine, based on analyzing the sensor data and the floor sensor data, an occupancy of a portion of the property;
        determine that the occupancy of the portion of the property exceeds a threshold occupancy of the property; and
        in response to determining that the occupancy of the portion of the property exceeds the threshold occupancy of the property, perform a monitoring system action.

2. The monitoring system of claim 1, wherein the monitor control unit is configured to:
    detect, based on analyzing the sensor data and the floor sensor data, one or more footsteps taken on the portion of the floor by a person; and
    generate footstep data, the footstep data comprising one or more of:
        a number of footsteps taken on the portion of the floor during a period of time;
        a path of footsteps taken on the portion of the floor during the period of time;
        a gait pattern of the person;
        a weight of the person; or
        a foot size of the person.

3. The monitoring system of claim 2, wherein the monitor control unit is configured to:
    determine, based on the footstep data, that the number of footsteps taken on the portion of the floor during the period of time deviates from an expected number of footsteps taken on the portion of the floor during the period of time; and
    communicate, to a user device of a user, a notification indicating that the number of footsteps taken on the portion of the floor during the period of time deviates from the expected number of footsteps taken on the portion of the floor during the period of time.

4. The monitoring system of claim 1, wherein the floor sensor is integrated into a floor surface, the floor surface comprising one or more of a tile, a carpet, a mat, a floorboard, a pad, or an underlayment.

5. The monitoring system of claim 1, wherein:
    the floor of the property comprises a plurality of tiles, and
    the floor sensor comprises:
        a plurality of pressure sensors, each of the plurality of pressure sensors integrated into a respective tile of the plurality of tiles and configured to output a measured amount of pressure applied to the respective tile.

6. The monitoring system of claim 1, wherein the floor sensor comprises one or more of a strain gauge, a fiber optic sensor, or a capacitive sensor.

7. The monitoring system of claim 1, wherein the amount of pressure applied to the portion of the floor of the property comprises an indication of either a presence or absence of pressure applied to the portion of the floor.

8. The monitoring system of claim 1, wherein the monitoring system action comprises activating one or more cameras to capture an image of an area of the property that includes the portion of the floor.

9. The monitoring system of claim 8, wherein the monitoring system action comprises:
identifying, using image analysis, a presence of a person in the image; and
determining, based on analyzing the floor sensor data, a predicted weight of the person in the image.

10. A method, comprising:
receiving, from a floor sensor, first floor sensor data that indicates an amount of pressure applied to a portion of a floor at a first time;
determining, using the first floor sensor data, an amount of pressure applied to the portion of the floor by a furnishing supporting a plurality of items;
receiving, from the floor sensor, second floor sensor data that indicates an amount of pressure applied to the portion of the floor at a second time;
detecting, using the second floor sensor data, a reduction in the amount of pressure applied to the portion of the floor by the furnishing between the first time and the second time;
in response to detecting the reduction in the amount of pressure applied to the portion of the floor by the furnishing, determining that one or more of the plurality of items has been removed from the furnishing; and
in response to determining that the one or more of the plurality of items has been removed from the furnishing,
performing a monitoring system action.

11. The method of claim 10, comprising:
detecting, based on analyzing the first floor sensor data and the second floor sensor data, one or more footsteps taken on the portion of the floor by a person; and
generating footstep data, the footstep data comprising one or more of:
a number of footsteps taken on the portion of the floor during a period of time;
a path of footsteps taken on the portion of the floor during the period of time;
a gait pattern of the person;
a weight of the person; or
a foot size of the person.

12. The method of claim 10, wherein the floor sensor is integrated into a floor surface, the floor surface comprising one or more of a tile, a carpet, a mat, a floorboard, a pad, or an underlayment.

13. The method of claim 10, wherein:
the floor comprises a plurality of tiles, and
the floor sensor comprises:
a plurality of pressure sensors, each of the plurality of pressure sensors integrated into a respective tile of the plurality of tiles and configured to output a measured amount of pressure applied to the respective tile.

14. The method of claim 10, wherein the floor sensor comprises one or more of a strain gauge, a fiber optic sensor, or a capacitive sensor.

15. The method of claim 10, wherein the amount of pressure applied to the portion of the floor comprises an indication of either a presence or absence of pressure applied to the portion of the floor.

16. The method of claim 10, wherein the monitoring system action comprises activating one or more cameras to capture an image of an area of a property that includes the portion of the floor.

17. The method of claim 16, wherein the monitoring system action comprises:
identifying, using image analysis, a presence of a person in the image; and
determining, based on analyzing the first floor sensor data and the second floor sensor data, a predicted weight of the person in the image.

18. One or more non-transitory computer storage media encoded with instructions that, when executed by one or more computers, cause the one or more computers to perform operations comprising:
receiving, from a sensor, sensor data was generated by the sensor and that indicates an attribute of a property, wherein the sensor comprises one of a thermometer, a camera, a microphone, an appliance monitor, or a water flow meter, and the sensor data comprises one of temperature data, camera data, microphone data, appliance monitor data, or water flow meter data;
receiving, from a floor sensor, floor sensor data that was generated by the floor sensor and indicates an amount of pressure applied to a portion of a floor of the property;
analyzing the sensor data and the floor sensor data;
determining, based on analyzing the sensor data and the floor sensor data, that a person has fallen on the portion of the floor, including:
determining a distribution of the amount of pressure applied to the portion of the floor;
determining that the distribution of the amount of pressure applied to the portion of the floor indicates that a person is prone on the floor; and
determining that a length of time that the person is prone on the floor exceeds a threshold length of time; and
in response to determining that the person has fallen on the portion of the floor, performing a monitoring system action.

19. The one or more non-transitory computer storage media of claim 18, wherein determining that the person has fallen on the portion of the floor comprises:
determining an impact pressure applied to the portion of the floor; and
determining that the impact pressure applied to the portion of the floor exceeded a threshold impact pressure.

20. The one or more non-transitory computer storage media of claim 18, wherein the floor sensor is integrated into a floor surface, the floor surface comprising one or more of a tile, a carpet, a mat, a floorboard, a pad, or an underlayment.

21. The one or more non-transitory computer storage media of claim 18, wherein:
the floor of the property comprises a plurality of tiles, and
the floor sensor comprises:
a plurality of pressure sensors, each of the plurality of pressure sensors integrated into a respective tile of the plurality of tiles and configured to output a measured amount of pressure applied to the respective tile.

22. The one or more non-transitory computer storage media of claim 18, wherein the floor sensor comprises one or more of a strain gauge, a fiber optic sensor, or a capacitive sensor.

23. The one or more non-transitory computer storage media of claim 18, wherein the amount of pressure applied to the portion of the floor of the property comprises an indication of either a presence or absence of pressure applied to the portion of the floor.

24. The one or more non-transitory computer storage media of claim 18, wherein the monitoring system action comprises activating one or more cameras to capture an image of an area of the property that includes the portion of the floor.

25. The one or more non-transitory computer storage media of claim 24, wherein the monitoring system action comprises:
   identifying, using image analysis, a presence of a person in the image; and
   determining, based on analyzing the floor sensor data, a predicted weight of the person in the image.

26. A method, comprising:
   receiving, from a sensor, sensor data that was generated by the sensor and indicates an attribute of a property, wherein the sensor comprises one of a thermometer, a camera, a microphone, an appliance monitor, or a water flow meter, and the sensor data comprises one of temperature data, camera data, microphone data, appliance monitor data, or water flow meter data;
   receiving, from a floor sensor, floor sensor data that was generated by the floor sensor and indicates an amount of pressure applied to a portion of a floor of the property;
   analyzing the sensor data and the floor sensor data;
   determining, based on analyzing the sensor data and the floor sensor data, an occupancy of a portion of the property;
   determining that the occupancy of the portion of the property exceeds a threshold occupancy of the property; and
   in response to determining that the occupancy of the portion of the property exceeds the threshold occupancy of the property, performing a monitoring system action.

27. The method of claim 26, comprising:
   detecting, based on analyzing the sensor data and the floor sensor data, one or more footsteps taken on the portion of the floor by a person; and
   generating footstep data, the footstep data comprising one or more of:
      a number of footsteps taken on the portion of the floor during a period of time;
      a path of footsteps taken on the portion of the floor during the period of time;
      a gait pattern of the person;
      a weight of the person; or
      a foot size of the person.

28. The method of claim 26, wherein the floor sensor is integrated into a floor surface, the floor surface comprising one or more of a tile, a carpet, a mat, a floorboard, a pad, or an underlayment.

29. The method of claim 26, wherein:
   the floor of the property comprises a plurality of tiles, and the floor sensor comprises:
      a plurality of pressure sensors, each of the plurality of pressure sensors integrated into a respective tile of the plurality of tiles and configured to output a measured amount of pressure applied to the respective tile.

30. The method of claim 26, wherein the floor sensor comprises one or more of a strain gauge, a fiber optic sensor, or a capacitive sensor.

31. The method of claim 26, wherein the amount of pressure applied to the portion of the floor of the property comprises an indication of either a presence or absence of pressure applied to the portion of the floor.

32. The method of claim 26, wherein the monitoring system action comprises activating one or more cameras to capture an image of an area of the property that includes the portion of the floor.

* * * * *